(12) United States Patent
Fischer et al.

(10) Patent No.: US 7,183,238 B2
(45) Date of Patent: Feb. 27, 2007

(54) [1,2]-OXAZINE-3,5-DIONES

(75) Inventors: Reiner Fischer, Monheim (DE); Thomas Schenke, Gladbach (DE); Christoph Erdelen, deceased, late of Leichlingen (DE); by Angelika Lubos-Erdelen, legal representative, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 197 days.

(21) Appl. No.: 10/497,479

(22) PCT Filed: Nov. 27, 2002

(86) PCT No.: PCT/EP02/13382

§ 371 (c)(1), (2), (4) Date: Jun. 1, 2004

(87) PCT Pub. No.: WO03/048138

PCT Pub. Date: Jun. 12, 2003

(65) Prior Publication Data

US 2005/0070707 A1    Mar. 31, 2005

(30) Foreign Application Priority Data

Dec. 6, 2001 (DE) ................. 101 60 007

(51) Int. Cl.
C07D 413/10 (2006.01)
C07D 265/02 (2006.01)
A61K 31/5355 (2006.01)
A01N 43/86 (2006.01)

(52) U.S. Cl. ................. 504/196; 544/63; 544/71; 564/182; 514/228.8; 504/223

(58) Field of Classification Search ................. 544/63, 544/71; 564/182; 514/228.8; 504/223, 504/196
See application file for complete search history.

(56) References Cited

U.S. PATENT DOCUMENTS

| | | | |
|---|---|---|---|
| 5,336,662 A | 8/1994 | Lee | 504/223 |
| 5,565,410 A | 10/1996 | Lee | 504/223 |
| 5,622,917 A | 4/1997 | Fischer et al. | 504/283 |
| 5,728,831 A | 3/1998 | Lee | 544/63 |
| 5,780,626 A | 7/1998 | Lee | 544/63 |
| 5,830,826 A | 11/1998 | Fischer et al. | 504/195 |
| 5,847,211 A | 12/1998 | Fischer et al. | 564/123 |
| 5,859,024 A | 1/1999 | Hotson et al. | 514/299 |
| 5,968,947 A | 10/1999 | Urch et al. | 514/299 |
| 5,994,274 A | 11/1999 | Fischer et al. | 504/282 |
| 6,093,726 A | 7/2000 | Urch et al. | 514/299 |
| 6,110,872 A | 8/2000 | Lieb et al. | 504/284 |
| 6,114,374 A | 9/2000 | Lieb et al. | 514/424 |
| 6,140,358 A | 10/2000 | Lieb et al. | 514/425 |
| 6,172,255 B1 | 1/2001 | Fischer et al. | 560/24 |
| 6,174,894 B1 | 1/2001 | Urch et al. | 514/299 |
| 6,177,442 B1 | 1/2001 | Urch et al. | 514/299 |
| 6,251,830 B1 | 6/2001 | Fischer et al. | 504/251 |
| 6,255,342 B1 | 7/2001 | Lieb et al. | 514/533 |
| 6,271,180 B2 | 8/2001 | Lieb et al. | 504/292 |
| 6,291,474 B1 | 9/2001 | Brightwell et al. | 514/299 |
| 6,316,486 B1 | 11/2001 | Lieb et al. | 514/411 |
| 6,358,887 B1 | 3/2002 | Fischer et al. | 504/284 |
| 6,359,151 B2 | 3/2002 | Lieb et al. | 549/265 |
| 6,380,246 B1 | 4/2002 | Lieb et al. | 514/462 |
| 6,388,123 B1 | 5/2002 | Lieb et al. | 560/76 |
| 6,417,370 B1 | 7/2002 | Lieb et al. | 548/408 |
| 6,451,843 B1 | 9/2002 | Lieb et al. | 514/422 |
| 6,458,965 B1 | 10/2002 | Lieb et al. | 548/408 |
| 6,469,196 B2 | 10/2002 | Fischer et al. | 560/105 |
| 6,472,419 B1 | 10/2002 | Fischer et al. | 514/425 |
| 6,486,343 B1 | 11/2002 | Lieb et al. | 560/39 |
| 6,504,036 B1 | 1/2003 | Lieb et al. | 549/265 |
| 6,511,942 B1 | 1/2003 | Lieb et al. | 504/299 |
| 6,693,092 B2 | 2/2004 | Lieb et al. | 514/183 |
| 6,716,832 B2 | 4/2004 | Lieb et al. | 514/183 |
| 2001/0004629 A1 | 6/2001 | Lieb et al. | 504/292 |

(Continued)

FOREIGN PATENT DOCUMENTS

| | | |
|---|---|---|
| EP | 0 394 889 | 10/1990 |
| EP | 0 508 126 | 10/1992 |
| WO | 92/07837 | 5/1992 |
| WO | 01/17972 | 3/2001 |

OTHER PUBLICATIONS

J. Org. Chem., 63 (month unavailable) 1998, pp. 5547-5554, Ned A. Porter et al, "Preparation of Unsymmetrically Labeled Hydroperoxides. A. Hydroxamate Ester-Nitrosation Approach".

(Continued)

Primary Examiner—Kahsay Habte
(74) Attorney, Agent, or Firm—Richard E. L. Henderson

(57) ABSTRACT

The present invention relates to novel [1,2]-oxazine-3,5-dione derivatives of the formula (I)

(I)

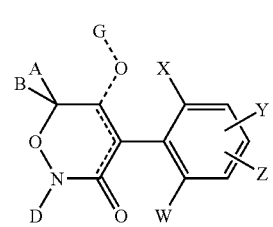

in which
W, X, Y, Z, G, D, A and B are as defined in the disclosure, to a plurality of processes for their preparation, and to their use as microbicides, pesticides and herbicides.

11 Claims, No Drawings

U.S. PATENT DOCUMENTS

| | | | |
|---|---|---|---|
| 2002/0010204 A1 | 1/2002 | Lieb et al. | 514/424 |
| 2002/0022575 A1 | 2/2002 | Fischer et al. | 504/221 |
| 2002/0061913 A1 | 5/2002 | Urch et al. | 514/366 |
| 2002/0188136 A1 | 12/2002 | Lieb et al. | 548/368.4 |
| 2003/0045432 A1 | 3/2003 | Fischer et al. | 504/221 |
| 2003/0073851 A1 | 4/2003 | Lieb et al. | 548/366.4 |
| 2003/0096806 A1 | 5/2003 | Lieb et al. | 514/212.01 |
| 2003/0144504 A1 | 7/2003 | Fischer et al. | 544/54 |
| 2003/0171219 A1 | 9/2003 | Lieb et al. | 504/221 |
| 2003/0199572 A1 | 10/2003 | Lieb et al. | 514/451 |
| 2004/0019061 A1 | 1/2004 | Fischer et al. | 514/256 |

OTHER PUBLICATIONS

Bull, Korean Chem. Soc., vol. 20, No. 8, (month unavailable) 1999, Kyukwan Zong et al, pp. 965-968, "A Facile Synthesis of [1,2]Oxazinane-3-5-diones".

Chem. Ind., 37, (month unavailable) 1985, pp. 730-732, Harry R. Ungerer, "Schiffstarben—eine Spezialität der seenahen Lackindustrie".

Chemical Reviews, 52, (month unavailable) 1953, pp. 237-416, Norman O.V. Sonntaf, "The Reactions of Aliphatic Acid Chlorides".

Indian J. Chem., 6, (month unavailable) 1968, pp. 341-345, Bhabatosh Bhattacharya, "Isoquinoline Derivatives: Part XVIII-Formation of I-Alky-(or alkaryl or aryl)-3-methyl-7-chloro-(or 5-chloro)-isoquinolines".

[1,2]-OXAZINE-3,5-DIONES

The present patent application has been filed under 35 U.S.C. 371 as a national stage application of PCT/EP02/13382, filed Nov. 27, 2002, which was published in German as International Patent Publication WO 03/048138 on Jun. 12, 2003, which is entitled to the right of priority of German Patent Application 101 60 007.0, filed Dec. 6, 2001.

The present invention relates to novel [1,2]-oxazine-3,5-dione derivatives and their enols, to a plurality of processes for their preparation and to their use as microbicides, pesticides and herbicides.

4-Phenyl-substituted [1,2]-oxazine-3,5-diones were described as herbicides for the first time in WO 01/17972. Furthermore, 4-acyl-substituted [1,2]-oxazine-3,5-diones were described as pesticides and in particular as herbicides and growth regulators, for example in EP-A-39 48 89, WO 92/07837, U.S. Pat. No. 5,728,831.

This invention now provides novel compounds of the formula (I)

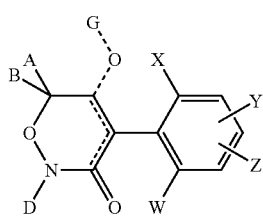

(I)

in which

W represents hydrogen, halogen, alkyl or alkoxy,

X represents halogen, alkyl, alkoxy, haloalkyl, haloalkoxy or cyano,

Y in the 4-position represents hydrogen, alkoxy, halogen, cyano or haloalkyl,

Z in the 3- or 5-position represents hydrogen or alkyl,

W also represents hydrogen, halogen or alkyl,

X also represents halogen, alkyl, alkoxy, haloalkyl, haloalkoxy or cyano,

Y in the 4-position also represents in each case optionally substituted aryl or hetaryl, Z also represents hydrogen, W likewise represents hydrogen, halogen or alkyl, X likewise represents halogen, alkyl, alkoxy, haloalkyl, haloalkoxy or cyano, Z likewise in the 5-position represents in each case optionally substituted aryl or hetaryl, Y in the 4-position likewise represents hydrogen, alkyl or halogen, W moreover represents hydrogen, methyl, propyl, isopropyl or halogen, X moreover represents halogen, alkyl, alkoxy, haloalkyl, haloalkoxy or cyano, Z in the 3- or 5-position moreover represents hydrogen, halogen or alkyl, Y in the 4-position moreover represents hydrogen, halogen, alkyl, haloalkyl, cyano or haloalkoxy, A represents hydrogen, in each case optionally halogen-substituted alkyl, alkenyl, alkoxyalkyl, polyalkoxyalkyl, alkylthioalkyl, saturated or unsaturated, optionally substituted cycloalkyl in which optionally at least one ring atom is replaced by a heteroatom, B represents hydrogen, alkyl or alkoxyalkyl, or A and B together with the carbon atom to which they are attached represent a saturated or unsaturated, unsubstituted or substituted cycle which optionally contains at least one heteroatom, D represents hydrogen or an optionally substituted radical from the group consisting of alkyl, alkenyl, alkoxyalkyl, polyalkoxyalkyl, alkylthioalkyl, saturated or unsaturated cycloalkyl in which optionally one or more ring members are replaced by heteroatoms, G represents hydrogen (a) or represents a group

(b)

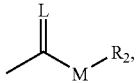
(c)

(d)

(e)

E or
(f)

(g)

where

E represents a metal ion equivalent or an ammonium ion,

L represents oxygen or sulphur,

M represents oxygen or sulphur, $R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, represents in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio, $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the N atom to which they are attached represent a cycle which is optionally interrupted by oxygen or sulphur.

Depending inter alia on the nature of the substituents, the compounds of the formula (I) can be present as geometrical and/or optical isomers or isomer mixtures of varying composition which, if desired, can be separated in a customary manner. The present invention provides both the pure isomers and the isomer mixtures, their preparation and use, and also compositions comprising them. However, hereinbelow, for the sake of simplicity, only compounds of the formula (I)

are referred to, although this is meant to be understood as including both the pure compounds and, if appropriate, mixtures with varying proportions of isomeric compounds.

Depending on the position of the substituent G, the compounds of the formula (I) can be present in the two isomeric forms of the formulae (I-A) and (I-B)

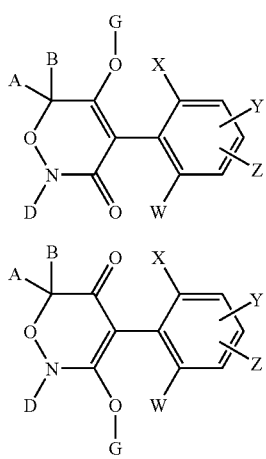

(I-A)

(I-B)

which is meant to be indicated by the broken line in formula (I).

The compounds of the formulae (I-A) and (I-B) can be present either as mixtures or in the form of their pure isomers. Mixtures of the compounds of the formulae (I-A) and (I-B) can, if desired, be separated in a manner known per se by physical methods, for example by chromatographic methods.

For the sake of improved clarity, hereinbelow only one of the possible isomers is shown in each case. This does not exclude the fact that the compounds may, if appropriate, be present in the form of the isomer mixtures or in the other respective isomeric form.

Including the different meanings (a), (b), (c), (d), (e), (f) and (g) of group G, the following principal structures (I-a) to (I-g) result (I-a):

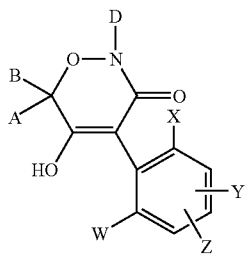

(I-b):

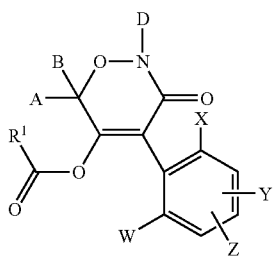

(I-c):

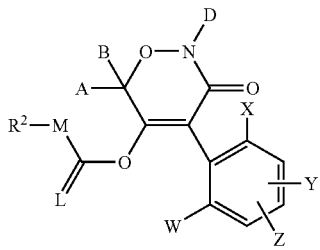

(I-d):

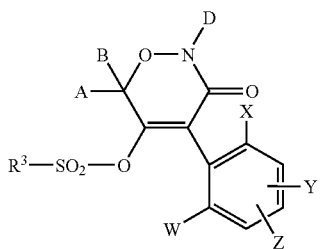

(I-e):

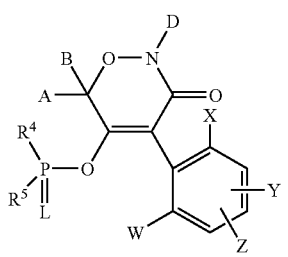

(I-f):

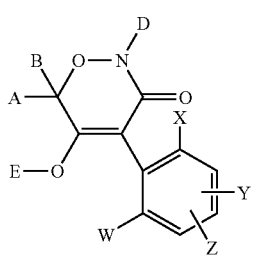

(I-g):

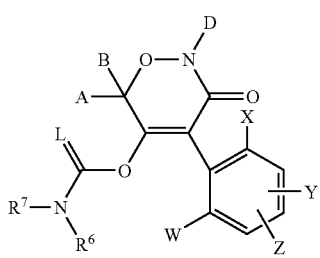

where

A, B, D, E, L, M, W, X, Y, Z, $R^1$, $R^2$, $R^3$, $R^4$, $R^5$, $R^6$ and $R^7$ are as defined above.

Furthermore, it has been found that the novel compounds of the formula (I) are obtained by one of the processes described below:

(A) substituted phenyl-1,2-oxazine-3,5-diones and their enols of the formula (I-a)

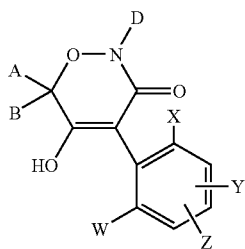

(I-a)

in which
A, B, D, W, X, Y and Z are as defined above,
are obtained when
N-acylhydroxyamino acid esters of the formula (II)

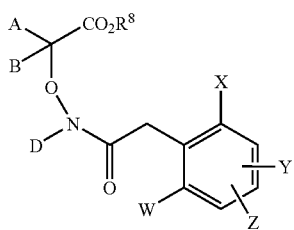

(II)

in which
A, B, D, W, X, Y and Z are as defined above
and
$R^8$ represents alkyl (preferably $C_1$–$C_6$-alkyl)
are condensed intramolecularly in the presence of a diluent and in the presence of a base.

Moreover, it has been found
(B) that compounds of the formula (I-b) shown above in which A, B, D, $R^1$, W, X, Y and Z are as defined above are obtained when compounds of the formula (I-a) shown above in which A, B, D, W, X, Y and Z are as defined above are in each case reacted (α) with acid halides of the formula (III)

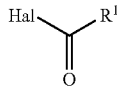

(III)

in which
$R^1$ is as defined above and
Hal represents halogen (in particular chlorine or bromine)
or
(β) with carboxylic anhydrides of the formula (IV)

$$R^1-CO-O-CO-R^1 \quad (IV)$$

in which
$R^1$ is as defined above,
if appropriate in the presence of a diluent and if appropriate in the presence of an acid binder;

(C) that compounds of the formula (I-c) shown above in which A, B, D, $R^2$, M, W, X, Y and Z are as defined above and L represents oxygen are obtained when compounds of the formula (I-a) shown above in which A, B, D, W, X, Y and Z are as defined above are in each case reacted with chloroformic esters or chloroformic thioesters of the formula (V)

$$R^2\text{-M-CO-Cl} \quad (V)$$

in which
$R^2$ and M are as defined above,
if appropriate in the presence of a diluent and if appropriate in the presence of an acid binder;

(D) that compounds of the formula (I-c) shown above in which A, B, D, $R^2$, M, W, X, Y and Z are as defined above and L represents sulphur are obtained when compounds of the formula (I-a) shown above in which A, B, D, W, X, Y and Z are as defined above are in each case reacted with chloromonothioformic esters or chlorodithioformic esters of the formula (VI)

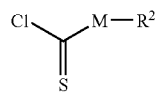

(VI)

in which
M and $R^2$ are as defined above,
if appropriate in the presence of a diluent and if appropriate in the presence of an acid binder;

(E) that compounds of the formula (I-d) shown above in which A, B, D, $R^3$, W, X, Y and Z are as defined above are obtained when compounds of the formula (I-a) shown above in which A, B, D, W, X, Y and Z are as defined above are in each case reacted with sulphonyl chlorides of the formula (VII)

$$R^3-SO_2-Cl \quad (VII)$$

in which
$R^3$ is as defined above,
if appropriate in the presence of a diluent and if appropriate in the presence of an acid binder, (F) that compounds of the formula (I-e) shown above in which A, B, D, L, $R^4$, $R^5$, W, X, Y and Z are as defined above are obtained when compounds of the formula (I-a) shown above in which A, B, D, W, X, Y and Z are as defined above are in each case reacted with phosphorus compounds of the formula (VIII)

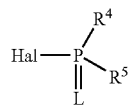

(VIII)

in which
L, $R^4$ and $R^5$ are as defined above and
Hal represents halogen (in particular chlorine or bromine),
if appropriate in the presence of a diluent and if appropriate in the presence of an acid binder, (G) that compounds of the formula (I-f) shown above in which A, B, D, E, W, X, Y and Z are as defined above are obtained when compounds of the formula (I-a) shown above in which A, B, D, W, X, Y and Z are as defined above are in each case reacted with metal compounds or amines of the formulae (IX) and (X), respectively, $$Me(OR^{10})_t \quad (IX)$$

$$R^{10}\text{—}N(R^{11})\text{—}R^{12} \quad (X)$$

in which

Me represents a mono- or divalent metal (preferably an alkali metal or alkaline earth metal, such as lithium, sodium, potassium, magnesium or calcium), t represents the number 1 or 2 and $R^{10}$, $R^{11}$, $R^{12}$ independently of one another represent hydrogen or alkyl (preferably $C_1$–$C_8$-alkyl), if appropriate in the presence of a diluent, (H) that compounds of the formula (I-g) shown above in which A, B, D, L, $R^6$, $R^7$, W, X, Y and Z are as defined above are obtained when compounds of the formula (I-a) shown above in which A, B, D, W, X, Y and Z are as defined above are in each case reacted (α) with isocyanates or isothiocyanates of the formula (XI)

$$R^6\text{—}N\text{=}C\text{=}L \quad (XI)$$

in which $R^6$ and L are as defined above, if appropriate in the presence of a diluent and if appropriate in the presence of a catalyst, or (β) with carbamoyl chlorides or thiocarbamoyl chlorides of the formula (XII)

$$R^6\text{—}N(R^7)\text{—}C(\text{=}L)\text{—}Cl \quad (XII)$$

in which

L, $R^6$ and $R^7$ are as defined above, if appropriate in the presence of a diluent and if appropriate in the presence of an acid binder.

Furthermore, it has been found that the novel compounds of the formula (I) have very good activity as pesticides, preferably as insecticides, acaricides and herbicides.

The formula (I) provides a general definition of the compounds according to the invention. Preferred substituents or ranges of the radicals listed in the formulae mentioned above and below are illustrated below:

W preferably represents hydrogen, halogen, $C_1$–$C_6$-alkyl or $C_1$–$C_6$-alkoxy, X preferably represents halogen, $C_1$–$C_6$-alkyl, $C_1$–$C_6$-alkoxy, $C_1$–$C_4$-haloalkyl, $C_1$–$C_4$-haloalkoxy or cyano, Y is preferably located in the 4-position and represents hydrogen, $C_1$–$C_6$-alkoxy, halogen, cyano or $C_1$–$C_4$-haloalkyl, Z is preferably located in the 3- or 5-position and represents hydrogen or $C_1$–$C_6$-alkyl, W also preferably represents hydrogen, halogen or $C_1$–$C_6$-alkyl, X also preferably represents halogen, $C_1$–$C_6$-alkyl, $C_1$–$C_6$-alkoxy, $C_1$–$C_4$-haloalkyl, $C_1$–$C_4$-haloalkoxy or cyano, Y is also preferably located in the 4-position and represents the radicals Z also preferably represents hydrogen, $V^1$ also preferably represents hydrogen, halogen, $C_1$–$C_{12}$-alkyl, $C_1$–$C_6$-alkoxy, $C_1$–$C_6$-alkylthio, $C_1$–$C_6$-alkylsulphinyl, $C_1$–$C_6$-alkylsulphonyl, $C_1$–$C_4$-haloalkyl, $C_1$–$C_4$-haloalkoxy, nitro, cyano or represents phenyl, phenoxy, phenoxy-$C_1$–$C_4$-alkyl, phenyl-$C_1$–$C_4$-alkoxy, phenylthio-$C_1$–$C_4$-alkyl or phenyl-$C_1$–$C_4$-alkylthio, each of which is optionally mono- or polysubstituted by halogen, $C_1$–$C_6$-alkyl, $C_1$–$C_6$-alkoxy, $C_1$–$C_4$-haloalkyl, $C_1$–$C_4$-haloalkoxy, nitro or cyano, $V^2$ and $V^3$ independently of one another also preferably represent hydrogen, halogen, $C_1$–$C_6$-alkyl, $C_1$–$C_6$-alkoxy, $C_1$–$C_4$-haloalkyl or $C_1$–$C_4$-haloalkoxy, $V^1$ and $V^2$ together also preferably represent $C_3$–$C_4$-alkanediyl which may optionally be substituted by halogen and/or $C_1$–$C_2$-alkyl and which may optionally be interrupted by one or two oxygen atoms, W likewise preferably represents hydrogen, halogen or $C_1$–$C_6$-alkyl, X likewise preferably represents halogen, $C_1$–$C_6$-alkyl, $C_1$–$C_6$-alkoxy, $C_1$–$C_4$-haloalkyl, $C_1$–$C_4$-haloalkoxy or cyano, Z likewise preferably in the 5-position represents the radicals

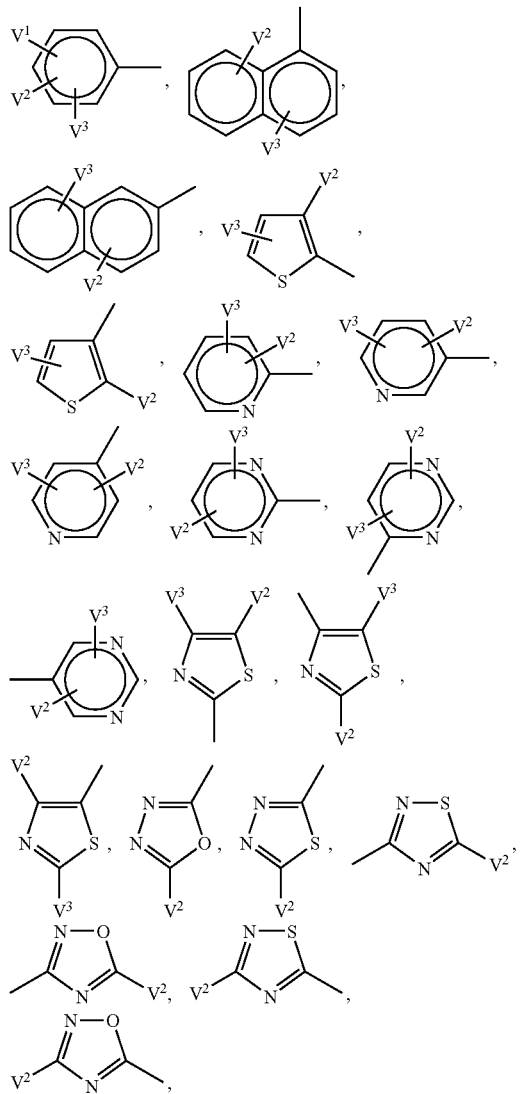

Y likewise preferably in the 4-position represents hydrogen, $C_1$–$C_6$-alkyl or halogen, $V^1$ likewise preferably represents hydrogen, halogen, $C_1$–$C_{12}$-alkyl, $C_1$–$C_6$-alkoxy, $C_1$–$C_6$-alkylthio, $C_1$–$C_6$-alkylsulphinyl, $C_1$–$C_6$-alkylsulphonyl, $C_1$–$C_4$-haloalkyl, $C_1$–$C_4$-haloalkoxy, nitro, cyano or represents phenyl, phenoxy, phenoxy-$C_1$–$C_4$-alkyl, phenyl-$C_1$–$C_4$-alkoxy, phenylthio-$C_1$–$C_4$-alkyl or phenyl-$C_1$–$C_4$-alkylthio, each of which is optionally mono- or polysubstituted by halogen, $C_1$–$C_6$-alkyl, $C_1$–$C_6$-alkoxy, $C_1$–$C_4$-haloalkyl, $C_1$–$C_4$-haloalkoxy, nitro or cyano, $V^2$ and $V^3$ likewise preferably independently of one another represent hydrogen, halogen, $C_1$–$C_6$-alkyl, $C_1$–$C_6$-alkoxy, $C_1$–$C_4$-haloalkyl or $C_1$–$C_4$-haloalkoxy, $V^1$ and $V^2$ together likewise preferably represent $C_3$–$C_4$-alkanediyl which may optionally be substituted by halogen and/or $C_1$–$C_2$-alkyl and which may optionally be interrupted by one or two oxygen atoms, W moreover preferably represents hydrogen, methyl, propyl, isopropyl or halogen, X moreover preferably represents halogen, $C_1$–$C_6$-alkyl, $C_1$–$C_6$-alkoxy, $C_1$–$C_4$-haloalkyl, $C_1$–$C_4$-haloalkoxy or cyano, Z moreover preferably in the 3- or 5-position represents hydrogen, halogen or $C_1$–$C_6$-alkyl, Y moreover preferably in the 4-position represents hydrogen, halogen, $C_1$–$C_6$-alkyl, $C_1$–$C_4$-haloalkyl, cyano or $C_1$–$C_4$-haloalkoxy, A preferably represents hydrogen or in each case optionally halogen-substituted $C_1$–$C_{12}$-alkyl, $C_3$–$C_8$-alkenyl, $C_1$–$C_{10}$-alkoxy-$C_1$–$C_8$-alkyl, poly-$C_1$–$C_8$-alkoxy-$C_1$–$C_8$-alkyl, $C_1$–$C_{10}$-alkylthio-$C_1$–$C_6$-alkyl, optionally halogen-, $C_1$–$C_6$-alkyl- or $C_1$–$C_6$-alkoxy-substituted $C_3$–$C_8$-cycloalkyl in which optionally one or two not directly adjacent ring members are replaced by oxygen and/or sulphur, B preferably represents hydrogen, $C_1$–$C_{12}$-alkyl or $C_1$–$C_8$-alkoxy-$C_1$–$C_6$-alkyl or A, B and the carbon atom to which they are attached preferably represent saturated $C_3$–$C_{10}$-cycloalkyl or unsaturated $C_5$–$C_{10}$-cycloalkyl in which optionally one ring member is replaced by oxygen or sulphur and which are optionally mono- or disubstituted by $C_1$–$C_8$-alkyl, $C_3$–$C_{10}$-cycloalkyl, $C_1$–$C_8$-haloalkyl, $C_1$–$C_8$-alkoxy, $C_1$–$C_8$-alkylthio, halogen or phenyl, D preferably represents hydrogen, in each case optionally halogen-substituted $C_1$–$C_{12}$-alkyl, $C_3$–$C_8$-alkenyl, $C_1$–$C_{10}$-alkoxy-$C_2$–$C_8$-alkyl, poly-$C_1$–$C_8$-alkoxy-$C_2$–$C_8$-alkyl, $C_1$–$C_{10}$-alkylthio-$C_2$–$C_8$-alkyl, optionally halogen-, $C_1$–$C_4$-alkyl-, $C_1$–$C_4$-alkoxy- or $C_1$–$C_4$-haloalkyl-substituted $C_3$–$C_8$-cycloalkyl in which optionally one ring member is replaced by oxygen or sulphur, G preferably represents hydrogen (a) or represents one of the groups

 (b)

 (c)

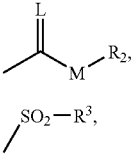 (d)

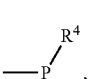 (e)

E or (f)

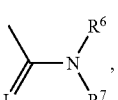 (g)

in particular (a), (b) or (c),
in which
E represents a metal ion equivalent or an ammonium ion, L represents oxygen or sulphur and M represents oxygen or sulphur, $R^1$ preferably represents in each case optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, poly-$C_1$–$C_8$-alkoxy-$C_1$–$C_8$-alkyl or optionally halogen-, $C_1$–$C_6$-alkyl- or $C_1$–$C_6$-alkoxy-substituted $C_3$–$C_8$-cycloalkyl in which optionally one or more (preferably not more than two) not directly adjacent ring members are replaced by oxygen and/or sulphur, represents optionally halogen-, cyano-, nitro-, $C_1$–$C_6$-alkyl-, $C_1$–$C_6$-alkoxy-, $C_1$–$C_6$-haloalkyl-, $C_1$–$C_6$-haloalkoxy-, $C_1$–$C_6$-alkylthio- or $C_1$–$C_6$-alkyl-sulphonyl-substituted phenyl, represents optionally halogen-, nitro-, cyano-, $C_1$–$C_6$-alkyl-, $C_1$–$C_6$-alkoxy-, $C_1$–$C_6$-haloalkyl- or $C_1$–$C_6$-haloalkoxy-substituted phenyl-$C_1$–$C_6$-alkyl, represents optionally halogen- or $C_1$–$C_6$-alkyl-substituted 5- or 6-membered hetaryl (for example pyrazolyl, thiazolyl, pyridyl, pyrimidyl, furanyl or thienyl), represents optionally halogen- or $C_1$–$C_6$-alkyl-substituted phenoxy-$C_1$–$C_6$-alkyl or represents optionally halogen-, amino- or $C_1$–$C_6$-alkyl-substituted 5- or 6-membered hetaryloxy-$C_1$–$C_6$-alkyl (for example pyridyloxy-$C_1$–$C_6$-alkyl, pyrimidyloxy-$C_1$–$C_6$-alkyl or thiazolyloxy-$C_1$–$C_6$-alkyl), $R^2$ preferably represents in each case optionally halogen-substituted $C_1$–$C_{20}$-alkyl, $C_2$–$C_{20}$-alkenyl, $C_1$–$C_8$-alkoxy-$C_2$–$C_8$-alkyl, poly-$C_1$–$C_8$-alkoxy-$C_2$–$C_8$-alkyl, represents optionally halogen-, $C_1$–$C_6$-alkyl- or $C_1$–$C_6$-alkoxy-substituted $C_3$–$C_8$-cycloalkyl or represents in each case optionally halogen-, cyano-, nitro-, $C_1$–$C_6$-alkyl-, $C_1$–$C_6$-alkoxy-, $C_1$–$C_6$-haloalkyl- or $C_1$–$C_6$-haloalkoxy-substituted phenyl or benzyl, $R^3$ preferably represents optionally halogen-substituted $C_1$–$C_8$-alkyl or represents in each case optionally halogen-, $C_1$–$C_6$-alkyl-, $C_1$–$C_6$-alkoxy-, $C_1$–$C_4$-haloalkyl-, $C_1$–$C_4$-haloalkoxy-, cyano- or nitro-substituted phenyl or benzyl, $R^4$ and $R^5$ independently of one another preferably represent in each case optionally halogen-substituted $C_1$–$C_8$-alkyl, $C_1$–$C_8$-alkoxy, $C_1$–$C_8$-alkylamino, di-($C_1$–$C_8$-alkyl) amino, $C_1$–$C_8$-alkylthio, $C_2$–$C_8$-alkenylthio, $C_3$–$C_7$-cycloalkylthio or represent in each case optionally halogen-, nitro-, cyano-, $C_1$–$C_4$-alkoxy-, $C_1$–$C_4$-haloalkoxy-, $C_1$–$C_4$-alkylthio-, $C_1$–$C_4$-haloalkylthio-, $C_1$–$C_4$-alkyl- or $C_1$–$C_4$-haloalkyl-substituted phenyl, phenoxy or phenylthio, $R^6$ and $R^7$ independently of one another preferably represent hydrogen, represent in each case optionally halogen-substituted $C_1$–$C_8$-alkyl, $C_3$–$C_8$-cycloalkyl, $C_1$–$C_8$-alkoxy, $C_3$–$C_8$-alkenyl, $C_1$–$C_8$-alkoxy-$C_1$–$C_8$-alkyl, represent optionally halogen-, $C_1$–$C_8$-haloalkyl-, $C_1$–$C_8$-alkyl- or $C_1$–$C_8$-alkoxy-substituted phenyl, optionally halogen-, $C_1$–$C_8$-alkyl-, $C_1$–$C_8$-haloalkyl- or $C_1$–$C_8$-alkoxy-substituted benzyl or together with the nitrogen atom to which they are attached represent optionally $C_1$–$C_4$-alkyl-substituted $C_4$–$C_7$-cycloalkyl in which optionally one carbon atom is replaced by oxygen or sulphur.

In the radical definitions mentioned as being preferred, halogen represents fluorine, chlorine, bromine and iodine, in particular fluorine, chlorine and bromine.

W particularly preferably represents hydrogen, chlorine, bromine, $C_1$–$C_4$-alkyl or $C_1$–$C_4$-alkoxy, X particularly preferably represents chlorine, bromine, $C_1$–$C_4$-alkyl, $C_1$–$C_4$-alkoxy, $C_1$–$C_2$-haloalkyl, $C_1$–$C_2$-haloalkoxy or cyano, Y particularly preferably in the 4-position represents hydrogen, $C_1$–$C_4$-alkoxy, chlorine, bromine, cyano or $C_1$–$C_2$-haloalkoxy, Z particularly preferably in the 3- or 5-position represents hydrogen or $C_1$–$C_4$-alkyl, W also particularly preferably represents hydrogen, chlorine, bromine or $C_1$–$C_4$-alkyl, X also particularly preferably represents chlorine, bromine, $C_1$–$C_4$-alkyl, $C_1$–$C_4$-alkoxy, $C_1$–$C_2$-haloalkyl, $C_1$–$C_2$-haloalkoxy or cyano, Y also particularly preferably in the 4-position represents the radicals

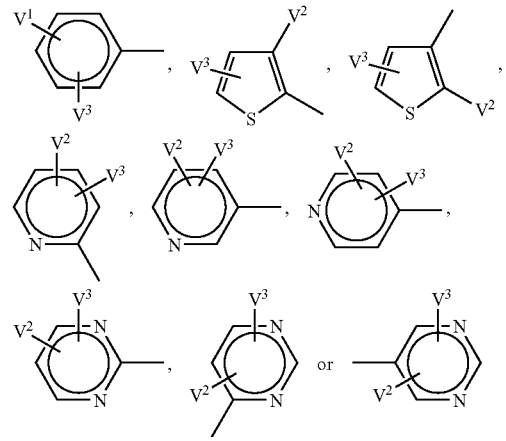

Z particularly preferably represents hydrogen, $V^1$ also particularly preferably represents hydrogen, fluorine, chlorine, bromine, $C_1$–$C_6$-alkyl, $C_1$–$C_4$-alkoxy, $C_1$–$C_2$-haloalkyl, $C_1$–$C_2$-haloalkoxy, nitro, cyano or phenyl which is in each case optionally mono- or disubstituted by fluorine, chlorine, bromine, $C_1$–$C_4$-alkyl, $C_1$–$C_4$-alkoxy, $C_1$–$C_2$-haloalkyl, $C_1$–$C_2$-haloalkoxy, nitro or cyano, $V^2$ and $V^3$ independently of one another also particularly preferably represent hydrogen, fluorine, chlorine, bromine, $C_1$–$C_4$-alkyl, $C_1$–$C_4$-alkoxy, $C_1$–$C_2$-haloalkyl or $C_1$–$C_2$-haloalkoxy, $V^1$ and $V^2$ together also particularly preferably represent —O—$CH_2$—O— or —O—$CF_2$—O—, W likewise particularly preferably represents hydrogen, chlorine, bromine or $C_1$–$C_4$-alkyl, X likewise particularly preferably represents chlorine, $C_1$–$C_4$-alkyl or $C_1$–$C_2$-haloalkyl, Z likewise particularly preferably in the 5-position represents the radicals

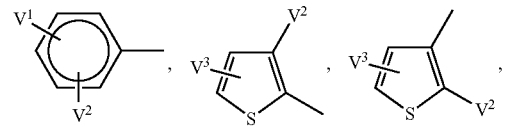

-continued

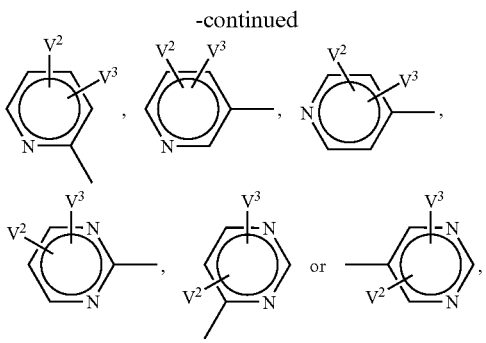

Y likewise particularly preferably in the 4-position represents hydrogen, $C_1$–$C_4$-alkyl or chlorine, $V^1$ likewise particularly preferably represents hydrogen, fluorine, chlorine, bromine, $C_1$–$C_6$-alkyl, $C_1$–$C_4$-alkoxy, $C_1$–$C_2$-haloalkyl, $C_1$–$C_2$-haloalkoxy, nitro, cyano or represents phenyl which is optionally mono- or disubstituted by fluorine, chlorine, bromine, $C_1$–$C_4$-alkyl, $C_1$–$C_4$-alkoxy, $C_1$–$C_2$-haloalkyl, $C_1$–$C_2$-haloalkoxy, nitro or cyano, $V^2$ and $V^3$ likewise independently of one another particularly preferably represent hydrogen, fluorine, chlorine, bromine, $C_1$–$C_4$-alkyl, $C_1$–$C_4$-alkoxy, $C_1$–$C_2$-haloalkyl or $C_1$–$C_2$-haloalkoxy, $V^1$ and $V^2$ together likewise particularly preferably represent —O—$CH_2$—O— or —O—$CF_2$—O—, W moreover particularly preferably represents hydrogen, methyl, chlorine or bromine, X moreover particularly preferably represents chlorine, bromine, $C_1$–$C_4$-alkyl, $C_1$–$C_4$-alkoxy, $C_1$–$C_2$-haloalkyl, $C_1$–$C_2$-haloalkoxy or cyano, Z moreover particularly preferably in the 3- or 5-position represents hydrogen, chlorine, bromine or $C_1$–$C_4$-alkyl, Y moreover particularly preferably in the 4-position represents hydrogen, chlorine, bromine, $C_1$–$C_4$-alkyl, $C_1$–$C_2$-haloalkyl, cyano or $C_1$–$C_2$-haloalkoxy, A particularly preferably represents hydrogen, represents $C_1$–$C_{10}$-alkyl, $C_1$–$C_8$-alkoxy-$C_1$–$C_6$-alkyl, each of which is optionally mono- to trisubstituted by fluorine or chlorine, represents $C_3$–$C_7$-cycloalkyl which is optionally mono- or disubstituted by fluorine, chlorine, $C_1$–$C_4$-alkyl or $C_1$–$C_4$-alkoxy and in which optionally one ring member is replaced by oxygen or sulphur, B particularly preferably represents hydrogen or $C_1$–$C_6$-alkyl or A, B and the carbon atom to which they are attached particularly preferably represent saturated or unsaturated $C_5$–$C_7$-cycloalkyl in which optionally one ring member is replaced by oxygen or sulphur and which is optionally monosubstituted by $C_1$–$C_6$-alkyl, $C_5$–$C_8$-cycloalkyl, $C_1$–$C_3$-haloalkyl or $C_1$–$C_6$-alkoxy or D particularly preferably represents hydrogen, represents $C_1$–$C_{10}$-alkyl, $C_3$–$C_6$-alkenyl, $C_1$–$C_6$-alkoxy-$C_2$–$C_4$-alkyl or $C_1$–$C_4$-alkylthio-$C_2$–$C_4$-alkyl, each of which is optionally mono- to trisubstituted by fluorine or chlorine, represents optionally fluorine-, chlorine-, $C_1$–$C_4$-alkyl-, $C_1$–$C_4$-alkoxy- or $C_1$–$C_2$-haloalkyl-substituted $C_3$–$C_7$-cycloalkyl in which optionally one methylene group is replaced by oxygen or sulphur, G particularly preferably represents hydrogen (a) or represents one of the groups

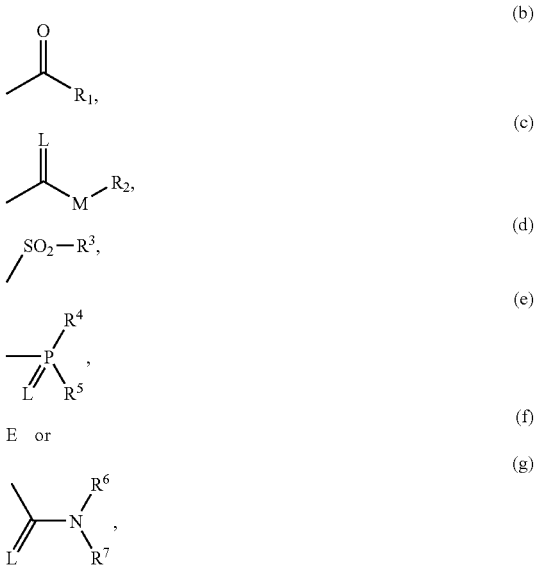

in particular (a), (b) or (c),
in which
E represents a metal ion equivalent or an ammonium ion,
L represents oxygen or sulphur and
M represents oxygen or sulphur, $R^1$ particularly preferably represents $C_1$–$C_{16}$-alkyl, $C_2$–$C_{16}$-alkenyl, $C_1$–$C_6$-alkoxy-$C_1$–$C_6$-alkyl, $C_1$–$C_4$-alkylthio-$C_1$–$C_4$-alkyl, poly-$C_1$–$C_4$-alkoxy-$C_1$–$C_4$-alkyl, each of which is optionally mono- to trisubstituted by fluorine or chlorine, or represents $C_3$–$C_7$-cycloalkyl which is optionally mono- or disubstituted by fluorine, chlorine, $C_1$–$C_4$-alkyl or $C_1$–$C_4$-alkoxy and in which optionally one or two not directly adjacent ring members are replaced by oxygen and/or sulphur, represents phenyl which is optionally mono- or disubstituted by fluorine, chlorine, bromine, cyano, nitro, $C_1$–$C_4$-alkyl, $C_1$–$C_4$-alkoxy, $C_1$–$C_3$-haloalkyl, $C_1$–$C_3$-haloalkoxy, $C_1$–$C_4$-alkylthio or $C_1$–$C_4$-alkylsulphonyl, represents phenyl-$C_1$–$C_4$-alkyl which is optionally mono- or disubstituted by fluorine, chlorine, bromine, $C_1$–$C_4$-alkyl, $C_1$–$C_4$-alkoxy, $C_1$–$C_3$-haloalkyl or $C_1$–$C_3$-haloalkoxy, represents pyrazolyl, thiazolyl, pyridyl, pyrimidyl, furanyl or thienyl, each of which is optionally monosubstituted by fluorine, chlorine, bromine or $C_1$–$C_4$-alkyl, represents phenoxy-$C_1$–$C_3$-alkyl which is optionally mono- or disubstituted by fluorine, chlorine, bromine or $C_1$–$C_4$-alkyl, $R^2$ particularly preferably represents $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, each of which is optionally mono- to trisubstituted by fluorine, represents $C_3$–$C_7$-cycloalkyl which is optionally mono- or disubstituted by fluorine, chlorine, $C_1$–$C_4$-alkyl or $C_1$–$C_4$-alkoxy or represents phenyl or benzyl, each of which is optionally mono- or disubstituted by fluorine, chlorine, bromine, cyano, nitro, $C_1$–$C_4$-alkyl, $C_1$–$C_3$-alkoxy, $C_1$–$C_3$-haloalkyl or $C_1$–$C_3$-haloalkoxy, $R^3$ particularly preferably represents $C_1$–$C_6$-alkyl which is optionally mono- to trisubstituted by fluorine or represents phenyl or benzyl, each of which is optionally mono- or disubstituted by fluorine, chlorine, bromine, $C_1$–$C_4$-alkyl, $C_1$–$C_4$-alkoxy, $C_1$–$C_3$-haloalkyl, $C_1$–$C_3$-haloalkoxy, cyano or nitro, $R^4$ particularly preferably represents $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio, $C_3$–$C_4$-alkenylthio, $C_3$–$C_6$-cycloalkylthio or represents phenyl, phenoxy or phenylthio, each of which is optionally mono- or disubstituted by fluorine, chlorine, bromine, nitro, cyano, $C_1$–$C_3$-alkoxy, $C_1$–$C_3$-haloalkoxy, $C_1$–$C_3$-alkylthio, $C_1$–$C_3$-haloalkylthio, $C_1$–$C_3$-alkyl or $C_1$–$C_3$-haloalkyl, $R^5$ particularly preferably represents $C_1$–$C_4$-alkoxy or $C_1$–$C_4$-alkylthio, $R^6$ particularly preferably represents $C_1$–$C_6$-alkyl, $C_3$–$C_6$-cycloalkyl, $C_1$–$C_6$-alkoxy, $C_3$–$C_6$-alkenyl, $C_1$–$C_6$-alkoxy-$C_1$–$C_6$-alkyl, represents phenyl which is optionally mono- or disubstituted by fluorine, chlorine, bromine, $C_1$–$C_3$-haloalkyl, $C_1$–$C_4$-alkyl or $C_1$–$C_4$-alkoxy, represents benzyl which is optionally mono- or disubstituted by fluorine, chlorine, bromine, $C_1$–$C_4$-alkyl, $C_1$–$C_3$-haloalkyl or $C_1$–$C_4$-alkoxy, $R^7$ particularly preferably represents hydrogen, $C_1$–$C_6$-alkyl or $C_3$–$C_6$-alkenyl, $R^6$ and $R^7$ together with the nitrogen atom to which they are attached particularly preferably represent $C_5$–$C_6$-cycloalkyl which is optionally mono- or disubstituted by methyl or ethyl and in which optionally one methylene group is replaced by oxygen or sulphur.

In the radical definitions mentioned as being particularly preferred, halogen represents fluorine, chlorine and bromine, in particular fluorine and chlorine.

W very particularly preferably represents hydrogen, chlorine, methyl, ethyl or methoxy, X very particularly preferably represents chlorine, bromine, methyl, ethyl, propyl, methoxy, trifluoromethyl, difluoromethoxy, trifluoroethoxy or cyano, Y very particularly preferably in the 4-position represents hydrogen, methoxy, chlorine, bromine or trifluoromethyl, Z very particularly preferably in the 3- or 5-position represents hydrogen or methyl, W also very particularly preferably represents hydrogen, chlorine, bromine or methyl, X also very particularly preferably represents chlorine, bromine, methyl, ethyl, propyl, methoxy, trifluoromethyl, difluoromethoxy or cyano, Y also very particularly preferably in the 4-position represents the radical

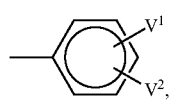

Z also very particularly preferably represents hydrogen, $V^1$ also very particularly preferably represents hydrogen, fluorine, chlorine, bromine, methyl, ethyl, n-propyl, isopropyl, tert-butyl, methoxy, ethoxy, n-propoxy, isopropoxy, trifluoromethyl or trifluoromethoxy, $V^2$ also very particularly preferably represents hydrogen, fluorine, chlorine, methyl, ethyl, n-propyl, isopropyl, methoxy, ethoxy or trifluoromethyl, W likewise very particularly preferably represents hydrogen, chlorine or methyl, X likewise very particularly preferably represents chlorine, methyl or trifluoromethyl, Z likewise very particularly preferably in the 5-position represents the radical

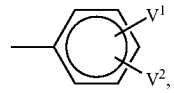

Y likewise very particularly preferably in the 4-position represents hydrogen or methyl, $V^1$ likewise very particularly preferably represents hydrogen, fluorine, chlorine, bromine, methyl, ethyl, n-propyl, isopropyl, tert-butyl, methoxy, ethoxy, n-propoxy, isopropoxy, trifluoromethyl or trifluoromethoxy, $V^2$ likewise very particularly preferably represents hydrogen, fluorine, chlorine, methyl, ethyl, n-propyl, isopropyl, methoxy, ethoxy or trifluoromethyl, W moreover very particularly preferably represents hydrogen, methyl, chlorine or bromine, X moreover very particularly preferably represents chlorine, bromine, methyl, methoxy, trifluoromethyl, difluoromethoxy, trifluoroethoxy or cyano, Z moreover very particularly preferably in the 3- or 5-position represents hydrogen, chlorine, bromine or methyl, Y moreover very particularly preferably in the 4-position represents hydrogen, chlorine, bromine, methyl, trifluoromethyl or trifluoromethoxy, A very particularly preferably represents hydrogen, $C_1$–$C_4$-alkyl or $C_1$–$C_4$-alkoxy-$C_1$–$C_2$-alkyl, or represents $C_3$–$C_6$-cycloalkyl which is optionally monosubstituted by fluorine, methyl, ethyl or methoxy and in which optionally one ring member is replaced by oxygen or sulphur, B very particularly preferably represents hydrogen, methyl or ethyl or A, B and the carbon atom to which they are attached very particularly preferably represent saturated $C_5$–$C_6$-cycloalkyl, in which optionally one ring member is replaced by oxygen and which is optionally monosubstituted by methyl, ethyl, propyl, isopropyl, butyl, trifluoromethyl, methoxy, ethoxy, propoxy, butoxy or isobutoxy, D very particularly preferably represents hydrogen, represents $C_1$–$C_8$-alkyl, $C_3$–$C_4$-alkenyl, $C_1$–$C_6$-alkoxy-$C_2$–$C_4$-alkyl, $C_1$–$C_4$-alkylthio-$C_2$–$C_4$-alkyl or $C_3$–$C_6$-cycloalkyl, each of which is optionally mono- to trisubstituted by fluorine, G very particularly preferably represents hydrogen (a) or represents one of the groups

(b)

(c)

(d)

(e)

E or (f)

-continued

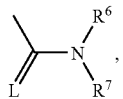
(g)

in particular (a), (b) or (c),
in which
E represents a metal ion equivalent or an ammonium ion,
L represents oxygen or sulphur and
M represents oxygen or sulphur,
$R^1$ very particularly preferably represents $C_1$–$C_{10}$-alkyl, $C_2$–$C_{10}$-alkenyl, $C_1$–$C_2$-alkoxy-$C_1$–$C_2$-alkyl, $C_1$–$C_2$-alkylthio-$C_1$–$C_2$-alkyl, each of which is optionally mono- to trisubstituted by fluorine or chlorine, or represents $C_3$–$C_6$-cycloalkyl which is optionally mono- or disubstituted by fluorine, chlorine, methyl, ethyl, propyl, i-propyl, butyl, i-butyl, tert-butyl, methoxy, ethoxy, n-propoxy or isopropoxy and in which optionally one ring member is replaced by oxygen,
represents phenyl which is optionally mono- or disubstituted by fluorine, chlorine, bromine, cyano, nitro, methyl, ethyl, n-propyl, i-propyl, tert-butyl, methoxy, ethoxy, trifluoromethyl or trifluoromethoxy,
represents benzyl which is optionally mono- or disubstituted by fluorine, chlorine, bromine, methyl, methoxy, trifluoromethyl or trifluoromethoxy,
represents furanyl, thienyl, pyridyl, pyrimidyl, thiazolyl or pyrazolyl, each of which is optionally substituted by fluorine, chlorine, bromine, methyl or ethyl,
$R^2$ very particularly preferably represents $C_1$–$C_{10}$-alkyl, $C_2$–$C_{10}$-alkenyl or $C_1$–$C_4$-alkoxy-$C_2$–$C_3$-alkyl, each of which is optionally mono- to trisubstituted by fluorine,
represents $C_3$–$C_6$-cycloalkyl which is optionally monosubstituted by fluorine, chlorine, methyl, ethyl or methoxy,
or represents phenyl or benzyl, each of which is optionally monosubstituted by fluorine, chlorine, cyano, nitro, methyl, ethyl, n-propyl, i-propyl, methoxy, ethoxy, trifluoromethyl or trifluoromethoxy,
$R^3$ very particularly preferably represents methyl, ethyl, n-propyl or represents phenyl which is optionally monosubstsituted by fluorine, chlorine, bromine, methyl, tert-butyl, methoxy, trifluoromethyl, trifluoromethoxy, cyano or nitro,
$R^4$ very particularly preferably represents $C_1$–$C_4$-alkyl, $C_1$–$C_4$-alkoxy, $C_1$–$C_4$-alkylamino, di-($C_1$–$C_4$-alkyl)amino, $C_1$–$C_4$-alkylthio or represents phenoxy or phenylthio, each of which is optionally monosubstituted by fluorine, chlorine, bromine, nitro, cyano, $C_1$–$C_2$-alkoxy, $C_1$–$C_2$-fluoroalkoxy, $C_1$–$C_2$-alkylthio, $C_1$–$C_2$-fluoroalkylthio or $C_1$–$C_3$-alkyl,
$R^5$ very particularly preferably represents methoxy, ethoxy, methylthio or ethylthio,
$R^6$ very particularly preferably represents $C_1$–$C_4$-alkyl, $C_3$–$C_6$-cycloalkyl, $C_1$–$C_4$-alkoxy, $C_3$–$C_4$-alkenyl, $C_1$–$C_4$-alkoxy-$C_1$–$C_4$-alkyl, represents phenyl which is optionally mono- or disubstituted by fluorine, chlorine, bromine, trifluoromethyl, methyl or methoxy, represents benzyl which is optionally monosubstituted by fluorine, chlorine, bromine, methyl, trifluoromethyl or methoxy,
$R^7$ very particularly preferably represents hydrogen, methyl, ethyl, propyl, isopropyl, butyl or allyl,
or $R^6$ and $R^7$ together with the nitrogen atom to which they are attached very particularly preferably represent $C_5$–$C_6$-cycloalkyl which is optionally mono- or disubstituted by methyl and in which optionally one methylene group is replaced by oxygen.
W especially preferably represents hydrogen, methyl, ethyl or chlorine,
X especially preferably represents methyl or chlorine,
Y especially preferably in the 4-position represents methoxy, chlorine, bromine or trifluoromethyl,
Z especially preferably in the 5-position represents hydrogen or methyl,
A especially preferably represents methyl,
B especially preferably represents methyl,
D especially preferably represents methyl or hydrogen, very especially preferably methyl,
G especially preferably represents hydrogen,
W likewise especially preferably represents hydrogen,
X likewise especially preferably represents methyl or chlorine,
Z likewise especially preferably in the 5-position represents

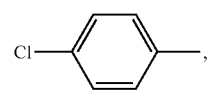

Y likewise especially preferably represents hydrogen,
A likewise especially preferably represents methyl,
B likewise especially preferably represents methyl,
A and B together likewise especially preferably represent —(CH$_2$)$_3$—,
D likewise especially preferably represents methyl,
G likewise especially preferably represents hydrogen (a) or represents one of the groups

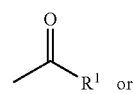
(b)

or

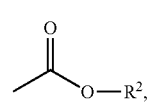
(c)

$R^1$ likewise especially preferably represents $C_1$–$C_6$-alkyl,
$R^2$ likewise especially preferably represents $C_1$–$C_6$-alkyl,
W moreover especially preferably represents hydrogen or methyl,
X moreover especially preferably represents methyl or bromine,
Z moreover especially preferably in the 3- or 5-position represents hydrogen or methyl,
Y moreover especially preferably in the 4-position represents methyl,
A moreover especially preferably represents methyl,
B moreover especially preferably represents methyl,
A and B together moreover especially preferably represent —(CH$_2$)$_4$—,
D moreover especially preferably represents methyl,
G moreover especially preferably represents hydrogen (a) or represents one of the groups

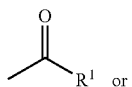 (b)

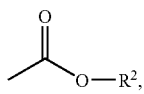 (c)

R[1] moreover especially preferably represents $C_1$–$C_6$-alkyl, R[2] moreover especially preferably represents $C_1$–$C_6$-alkyl.

The general or preferred radical definitions or illustrations listed above can be combined with one another as desired, i.e. including combinations between the respective ranges and preferred ranges. The definitions apply both to the end products and, correspondingly, to precursors and intermediates.

Preference according to the invention is given to compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Especially preferred according to the invention are the compounds of the formula (I) which contain a combination of the meanings listed above as being especially preferred.

Especially preferred are compounds of the formula (I) where Z represents optionally substituted aryl.

Saturated or unsaturated hydrocarbon radicals, such as alkyl or alkenyl, can in each case be straight-chain or branched as far as this is possible, including in combination with heteroatoms, such as, for example, in alkoxy.

Unless defined otherwise, optionally substituted radicals can be mono- or polysubstituted, where in the case of polysubstitutions the substituents can be identical or different.

Using, for example, according to process (A), ethyl N-methyl-N-[(6-methyl-3-phenyl)phenylacetyl]-1-aminooxycyclopentanecarboxylate as starting material, the course of the process according to the invention can be represented by the reaction scheme below:

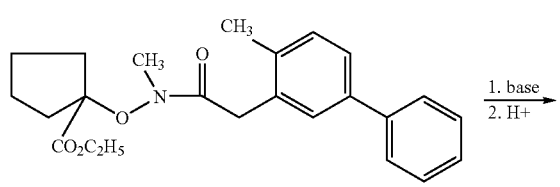

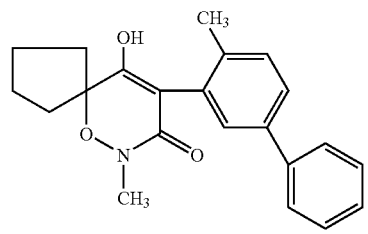

Using, for example, according to process (Bα), 2-methyl-4-[(2-chloro-5-(3-chlorophenyl))phenyl]-6,6-dimethyl-[1,2]-oxazine-3,5-dione and pivaloyl chloride as starting materials, the course of the process according to the invention can be represented by the reaction scheme below:

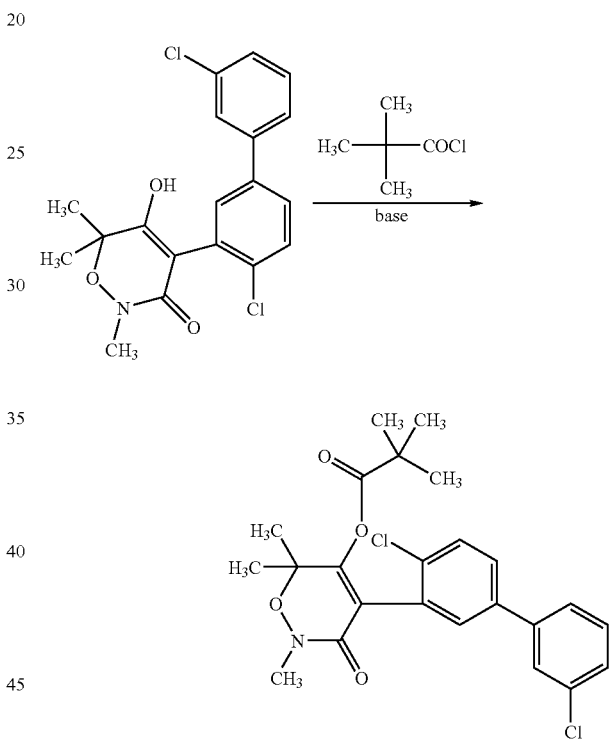

Using, for example, according to process (B) (variant β), 2-ethyl-4-(2,5-dimethylphenyl)-6,6-dimethyl-[1,2]-oxazine-3,5-dione and acetic anhydride as starting materials, the course of the process according to the invention can be represented by the reaction scheme below:

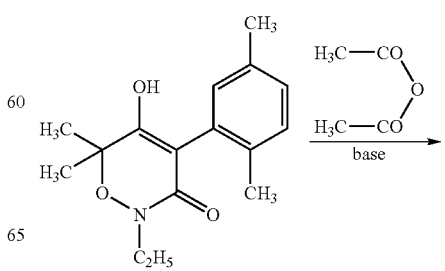

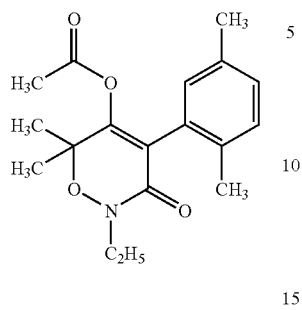

Using, for example, according to process (C), 2-methyl-4-(2,4,6-trimethylphenyl)-6,6-dimethyl-[1,2]-oxazine-3,5-dione and ethoxyethyl chloroformate as starting materials, the course of the process according to the invention can be represented by the reaction scheme below:

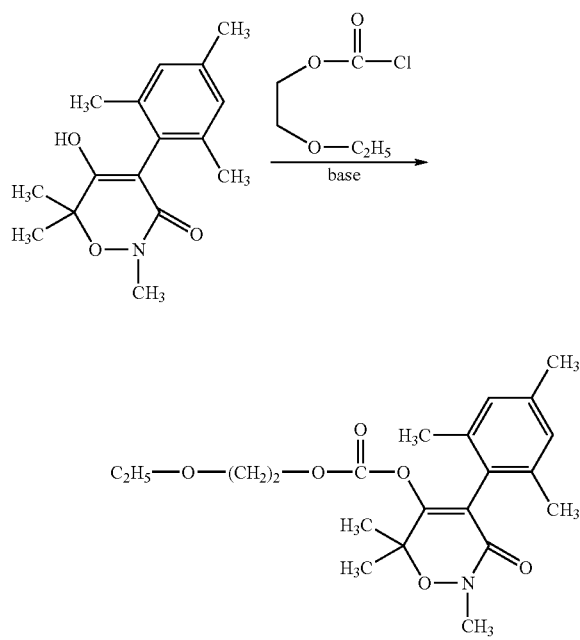

Using, for example, according to process (D), 2-methyl-4-(2,5-dichlorophenyl)-6,6-dimethyl-[1,2]-oxazine-3,5-dione and methyl chloromonothioformate as starting materials, the course of the reaction can be represented as follows:

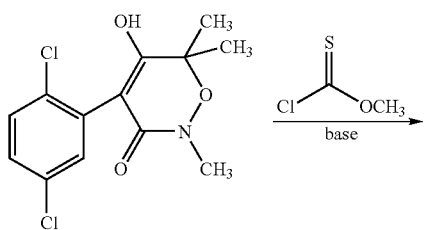

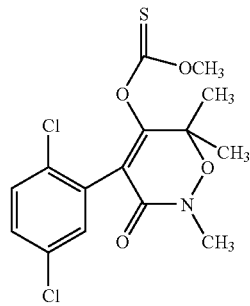

Using, for example, according to process (E), 2-methyl-4-(2,4,6-trimethylphenyl)-6,6-pentamethylene-[1,2]-oxazine-3,5-dione and methanesuphonyl chloride as starting materials, the course of the reaction can be represented by the reaction scheme below:

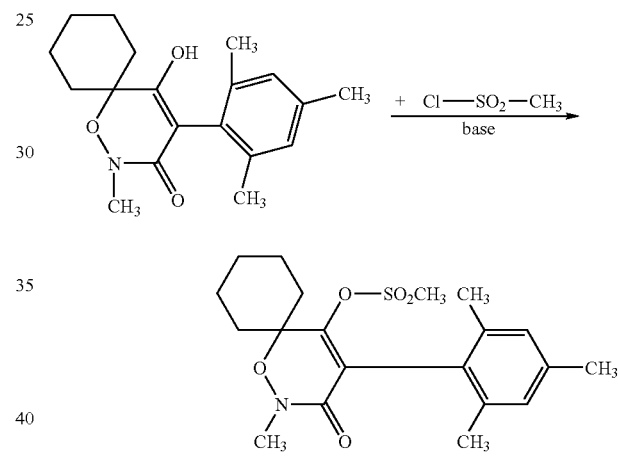

Using, for example, according to process (F), 2-methyl-4-(4-chloro-2,6-dimethylphenyl)-6,6-dimethyl-[1,2]-oxazine-3,5-dione and 2,2,2-trifluoroethyl methanethiophosphonyl chloride as starting materials, the course of the reaction can be represented by the reaction scheme below:

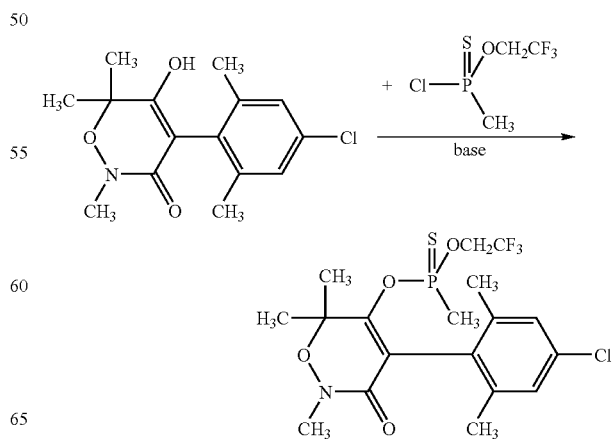

Using, for example, according to process (G), 2-methyl-4-[2-methyl-5-(4-chlorophenyl)phenyl]-6,6-dimethyl-[1,2]-oxazine-3,5-dione and NaOH as components, the course of the process according to the invention can be represented by the reaction scheme below:

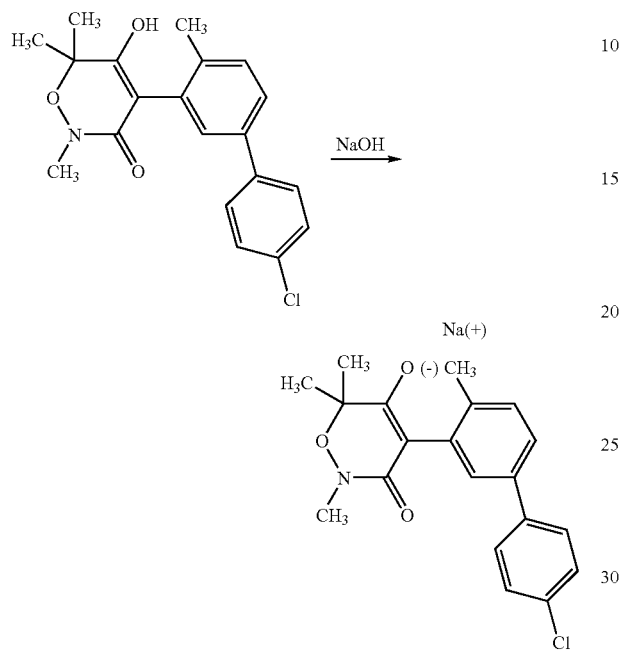

Using, for example, according to process (H) (variant α), 2-methyl-5-(2,4-dimethylphenyl)-6,6-pentamethylene-[1,2]-oxazine-3,5-dione and ethyl isocyanate as starting materials, the course of the reaction can be represented by the reaction scheme below:

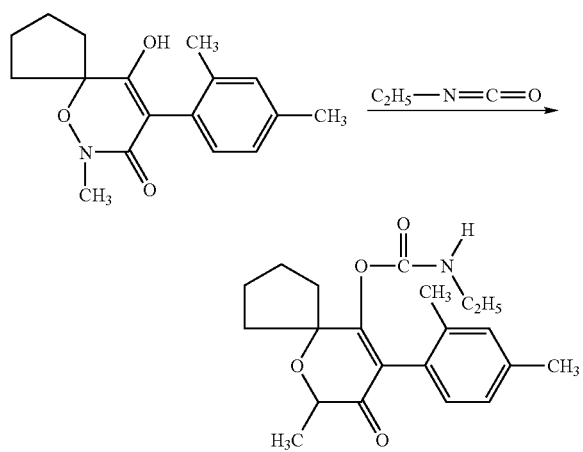

Using, for example, according to process (H) (variant β), 2-methyl-4-[2-chloro-5-(4-chlorophenyl)phenyl]-6,6-dimethyl-[1,2]-oxazine-3,5-dione and dimethylcarbamoyl chloride as starting materials, the course of the reaction can be represented by the scheme below:

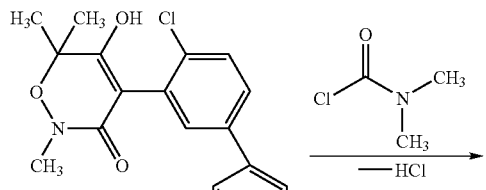

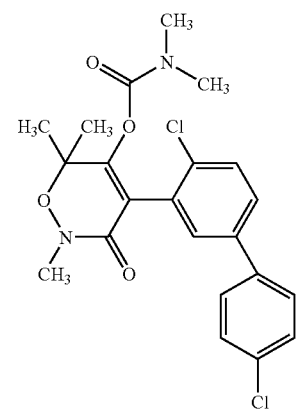

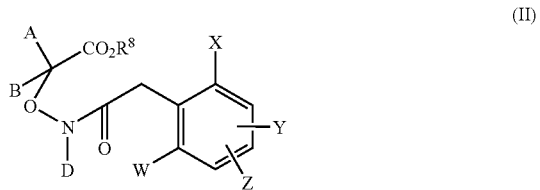

The compounds, required as starting materials in the process (a) according to the invention, of the formula (II)

(II)

in which
A, B, D, W, X, Y, Z and $R^8$ are as defined above,
are novel.

The acylhydroxylamino acid esters of the formula (II) are obtained, for example, when amino acid derivatives of the formula (XIII)

(XIII)

in which
A, B, $R^8$ and D are as defined above,
are acylated with substituted phenylacetyl halides of the formula (XIV)

(XIV)

in which

W, X, Y and Z are as defined above und

Hal represents chlorine or bromine (Chem. Reviews 52, 237–416 (1953); Bhattacharya, Indian J. Chem. 6, 341–5, 1968).

Some of the hydroxylamino acid esters, required as starting materials for preparing compounds of the formula (II), of the formula (XIII)

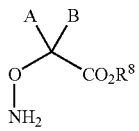

(XIII)

in which

A, B and R$^8$ are as defined above are novel, and they can be prepared by known processes (N. A. Porter et al. J. Org. Chem. 63 5547 (1998)).

Thus, hydroxylamino acid esters of the formula (XIII)

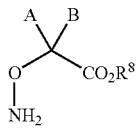

(XIII)

in which

A, B and R$^8$ are as defined above are obtained, for example, when N-hydroxyphthalimide of the formula (XV)

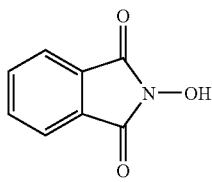

(XV)

is reacted with haloalkyl esters of the formula (XVI)

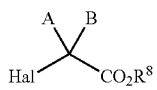

(XVI)

in which

A, B and R$^8$ are as defined above and

Hal represents chlorine, bromine or iodine, preferably bromine, to give O-alkoxyphthalimides of the formula (XVII),

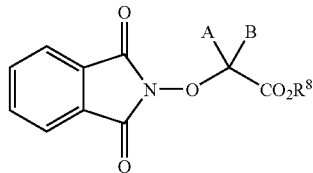

(XVII)

in which

A, B and R$^8$ are as defined above and the compounds of the formula (XIII-a) are released from these compounds by hydrazinolysis, for example.

Most of the phenylacetyl halides, required for preparing the compounds (II), of the formula (XIV)

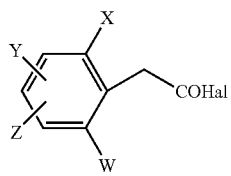

(XIV)

in which

W, X, Y and Z are as defined above and

Hal represents fluorine, chlorine or bromine, preferably chlorine, are known, or they can be prepared by known processes (WO 95/20572, EP-A 668 267, WO 95/26954, WO 96/25395, WO 96/35664, WO 97/02243, WO 97/01535, WO 97/36868, WO 98/05638, WO 99/43649, WO 99/48869, WO 99/55673).

The compounds of the formulae (XVI) and (XV) are likewise known and can be prepared by known processes (N. A. Porter et al. J. Org. Chem. 63, 5547–5554, 1998).

Furthermore, acylhydroxylamino acid esters of the formula (II)

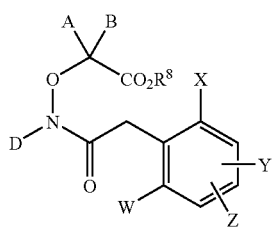

(II)

in which

A, B, D, W, X, Y, Z and R$^8$ are as defined above, but where D is preferably not hydrogen are obtained, for example, when phenylacetyl halides of the formula (XIV)

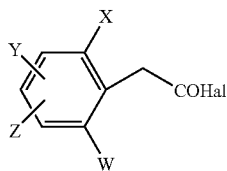

(XIV)

in which

W, X, Y and Z are as defined above and

Hal represents fluorine, chlorine or bromine, preferably chlorine, are reacted with hydroxylamines of the formula (XVIII)

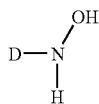

(XVIII)

in which

D is as defined above, but is preferably not hydrogen, to give compounds of the formula (XIX)

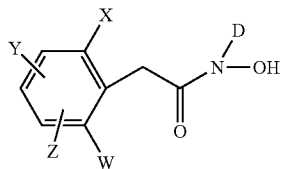

(XIX)

in which

D, W, X, Y and Z are as defined above, and these compounds are then alkylated with haloalkyl esters of the formula (XVI),

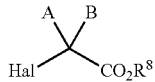

(XVI)

in which

A, B and $R^8$ are as defined above and

Hal represents chlorine, bromine and iodine, preferably bromine, to give compounds of the formula (II) (E. K. Ryo et al., Bull. Korean Chem. Soc. 20 965 (1999)).

Some of the compounds of the formula (XVIII) are commercially available, some are known, and they can be prepared by known processes.

Moreover, compounds of the formula (II) in which D is not hydrogen are obtained when compounds of the formula (II-a)

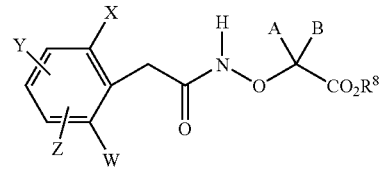

(II-a)

in which

A, B, W, X, Y, Z and $R^8$ are as defined above are alkylated with compounds of the formula (XX)

D-LG          (XX)

in which

D is as defined above, but is not hydrogen, and

LG is a leaving group, such as, for example, chlorine, bromine, iodine, mesylate, tosylate or triflate, to give compounds of the formula II (see Example II-3).

Some of the compounds of the formula (XX) are commercially available, some are known, and they can be prepared by known processes.

The acid halides of the formula (III), carboxylic anhydrides of the formula (IV), chloroformic esters or chloroformic thioesters of the formula (V), chloromonothioformic esters or chlorodithioformic esters of the formula (VI), sulphonyl chlorides of the formula (VII), phosphorus compounds of the formula (VIII) and metal hydroxides, metal alkoxides or amines of the formulae (IX) and (X), respectively, and isocyanates of the formula (XI) and carbamoyl chlorides of the formula (XII) furthermore required as starting materials for carrying out the processes (B), (C), (D), (E), (F), (G) and (H) according to the invention are generally known compounds of organic or inorganic chemistry.

The process (A) is characterized in that compounds of the formula (II) in which A, B, D, W, X, Y, Z and $R^8$ are as defined above are subjected to an intramolecular condensation in the presence of a base.

Suitable diluents for use in the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltri($C_8$–$C_{10}$)alkylammonium chloride) or TDA 1 (=tris(methoxyethoxyethyl)

amine). It is furthermore possible to use alkali metals, such as sodium or potassium. Also suitable are alkali metal and alkaline earth metal amides and hydrides, such as sodium amide, sodium hydride and calcium hydride, and furthermore also alkali metal alkoxides, such as sodium methoxide, sodium ethoxide and potassium tert-butoxide.

When carrying out the process (A) according to the invention, the reaction temperatures can be varied within a relatively wide range. In general, the process is carried out at temperatures between −78° C. and 250° C., preferably between 0° C. and 150° C.

The process (A) according to the invention is generally carried out under atmospheric pressure.

When carrying out the process (A) according to the invention, the reaction components of the formula (II) and the deprotonating bases are generally employed in approximately double-equimolar amounts. However, it is also possible to use a relatively large excess (up to 3 mol) of one component or the other.

The process (B-α) is characterized in that compounds of the formula (I-a) are in each case reacted with carbonyl halides of the formula (III), if appropriate in the presence of a diluent and if appropriate in the presence of an acid binder.

Suitable for use as diluents in the process (B-α) according to the invention are all solvents which are inert towards the acid halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane. The hydrolytic stability of the acid halide permitting, the reaction can also be carried out in the presence of water.

Acid binders suitable for the reaction according to process (B-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

When carrying out the process (B-α) according to the invention, the reaction temperatures can be varied within a relatively wide range. In general, the process is carried out at temperatures between −20° C. and +150° C., preferably between 0° C. and 100° C.

When carrying out the process (B-α) according to the invention, the starting materials of the formula (I-a) and the carbonyl halide of the formula (III) are generally each employed in approximately equivalent amounts. However, it is also possible to use a relatively large excess (up to 5 mol) of the carbonyl halide. Work-up is carried out by customary methods.

The process (B-β) is characterized in that compounds of the formula (I-a) are reacted with carboxylic anhydrides of the formula (IV), if appropriate in the presence of a diluent and if appropriate in the presence of an acid binder.

Diluents suitable for use in the process (B-β) according to the invention are preferably those diluents which are also preferred when acid halides are used. Besides, a carboxylic anhydride employed in excess may simultaneously act as diluent.

Preferred acid binders which are, if appropriate, employed in process (B-β) are those acid binders which are also preferred when acid halides are used.

When carrying out the process (B-β) according to the invention, the reaction temperatures can be varied within a relatively wide range. In general, the process is carried out at temperatures between −20° C. and +150° C., preferably between 0° C. and 100° C.

When carrying out the process (B-β) according to the invention, the starting materials of the formula (I-a) and the carboxylic anhydride of the formula (IV) are generally each employed in approximately equivalent amounts. However, it is also possible to use a relatively large excess (up to 5 mol) of the carboxylic anhydride. Work-up is carried out by customary methods.

In general, diluent and excess carboxylic anhydride and the carboxylic acid formed are removed by distillation or by washing with an organic solvent or with water.

The process (C) is characterized in that compounds of the formula (I-a) are in each case reacted with chloroformic esters or chloroformic thioesters of the formula (V), if appropriate in the presence of a diluent and if appropriate in the presence of an acid binder.

Acid binders suitable for the reacton of process (C) according to the invention are all customary acid acceptors. Preference is given to using tertiary amines, such as triethylamine, pyridine, DABCO, DBU, DBA, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Diluents suitable for the process (C) according to the invention are all solvents which are inert towards the chloroformic esters or chloroformic thioesters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane.

When carrying out the process (C) according to the invention, the reaction temperatures can be varied within a relatively wide range. If the process is carried out in the presence of a diluent and an acid binder, the reaction temperatures are generally between −20° C. and +100° C., preferably between 0° C. and 50° C.

The process (C) according to the invention is generally carried out under atmospheric pressure.

When carrying out the process (C) according to the invention, the starting materials of the formula (I-a) and the appropriate chloroformic ester or chloroformic thioester of the formula (V) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent.

The process (D) according to the invention is characterized in that compounds of the formula (I-a) are in each case reacted with compounds of the formula (VI), in the presence of a diluent and, if appropriate, in the presence of an acid binder.

In the preparation process (D), about 1 mol of chloromonothioformic ester or chlorodithioformic ester of the formula (VI) is reacted per mole of starting material of the formula (I-a), at from 0 to 120° C., preferably from 20 to 60° C.

Suitable diluents, which are added, if appropriate, are all inert polar organic solvents, such as ethers, amides, sulphones, sulphoxides, and also halogenated alkanes.

Preference is given to using dimethyl sulphoxide, tetrahydrofuran, dimethylformamide or methylene chloride.

If, in a preferred embodiment, the enolate salt of the compounds (I-a) is prepared by addition of strong deprotonating agents, such as, for example, sodium hydride or potassium tert-butoxide, the further addition of acid binders may be dispensed with.

If acid binders are used, these are customary inorganic or organic bases, for example sodium hydroxide, sodium carbonate, potassium carbonate, pyridine or triethylamine.

The reaction can be carried out at atmospheric pressure or under elevated pressure and is preferably carried out at atmospheric pressure. Work-up is by customary methods.

Process (E) according to the invention is characterized in that compounds of the formula (I-a) are in each case reacted with sulphonyl chlorides of the formula (VII), if appropriate in the presence of a diluent and if appropriate in the presence of an acid binder.

In the preparation process (E), about 1 mol of sulphonyl chloride of the formula (VII) is reacted per mole of starting material of the formula (I-a), at from −20 to 150° C., preferably from 20 to 70° C.

Suitable diluents which are added, if appropriate, are all inert polar organic solvents, such as ethers, amides, nitriles, sulphones, sulphoxides or halogenated hydrocarbons, such as methylene chloride.

Preference is given to using dimethyl sulphoxide, tetrahydrofuran, dimethylformamide or methylene chloride.

If, in a preferred embodiment, the enolate salt of the compounds (I-a) is prepared by addition of strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, pyridine or triethylamine.

The reaction can be carried out at atmospheric pressure or under elevated pressure and is preferably carried out at atmospheric pressure. Work-up is by customary methods.

The process (F) according to the invention is characterized in that compounds of the formula (I-a) are in each case reacted with phosphorus compounds of the formula (VIII), if appropriate in the presence of a diluent and, if appropriate, in the presence of an acid binder.

In the preparation process (F), 1 to 2, preferably 1 to 1.3, mol of the phosphorus compound of the formula (VIII) are reacted per mole of the compounds (I-a), at temperatures between −40° C. and 150° C., preferably between −10 and 110° C., to obtain compounds of the formula (I-e).

Suitable diluents, which are added, if appropriate, are all inert polar organic solvents, such as ethers, amides, nitriles, alcohols, sulphides, sulphones, sulphoxides, etc.

Preference is given to using acetonitrile, dimethyl sulphoxide, tetrahydrofuran, dimethylformamide or methylene chloride.

Suitable acid binders, which are added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods of organic chemistry. Purification of the resulting end products is preferably by crystallization, chromatographic purification or by "incipient distillation", i.e. removal of the volatile components under reduced pressure.

The process (G) is characterized in that compounds of the formula (I-a) are reacted with metal hydroxides or metal alkoxides of the formula (IX) or with amines of the formula (X), if appropriate in the presence of a diluent.

Preferred diluents for use in the process (G) according to the invention are ethers, such as tetrahydrofuran, dioxane or diethyl ether, or else alcohols, such as methanol, ethanol or isopropanol, and also water.

The process (G) according to the invention is generally carried out under atmospheric pressure.

The reaction temperatures are generally between −20° C. and 100° C., preferably between 0° C. and 50° C.

The process (H) according to the invention is characterized in that compounds of the forrmula (I-a) are in each case reacted with (H-α) compounds of the formula (XI), if appropriate in the presence of a diluent and if appropriate in the presence of a catalyst, or (H-β) with compounds of the formula (XII), if appropriate in the presence of a diluent and if appropriate in the presence of an acid binder.

In preparation process (H-α), about 1 mol of isocyanate of the formula (XI) is reacted per mole of starting material of the formula (I-a), at from 0 to 100° C., preferably from 20 to 50° C.

Suitable diluents which are added, if appropriate, are all inert organic solvents, such as ethers, amides, nitriles, sulphones, sulphoxides.

If appropriate, catalysts can be added to accelerate the reaction. Advantageously, the catalysts used are organotin compounds, such as, for example, dibutyltin dilaurate. The process is preferably carried out at atmospheric pressure.

In the preparation process (H-β), about 1 mol of carbamoyl chloride of the formula (XII) is reacted per mole of starting material of the formula (I-a), at from −20 to 150° C., preferably from 0 to 70° C.

Suitable diluents which are added, if appropriate, are all inert polar organic solvents, such as ethers, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compound (I-a) is prepared by addition of strong deprotonating agents (such as, for example, sodium hydride or potassium tert-butoxide), the further addition of acid binders can be dispensed with.

If acid binders are used, these are customary organic or inorganic bases, for example sodium hydroxide, sodium carbonate, potassium carbonate, triethylamine or pyridine.

The reaction can be carried out at atmospheric pressure or under elevated pressure and is preferably carried out at atmospheric pressure. Work-up is carried out by customary methods.

The active compounds are suitable for protecting plants and plant organs, for increasing the harvest yields, for improving the quality of the harvested goods and for controlling animal pests, in particular insects, arachnids and nematodes, which are encountered in agriculture, in forests, in gardens and leisure facilities, in the protection of stored products and of materials, and in the hygiene sector, and have good plant tolerance, favourable toxicity to warm-blooded animals and good environmental compatibility. They may be preferably employed as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumniferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Omithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats.

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is, liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

As solid carriers there are suitable:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be employed as such or in their formulations as a mixture with known fungicides, bactericides, acaricides, nematicides or insecticides in order for example to increase the activity spectrum or avoid the development of resistance. In many cases synergistic effects are achieved, ie. the efficacy of the mixture is greater than the efficacy of the individual components.

Favourable examples of co-components in mixtures are the following compounds:

Fungicides:

aldimorph, ampropylfos, ampropylfos-potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropirnorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, flircarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxirn, oxyfenthiin, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole,
validamycin A, vinclozolin, viniconazole,
zarilamide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)-ethanone-O-(phenylmethyl)-oxime,
1-(2-methyl-1-naphthalenyl)-1H-pyrrol-2,5-dione,
1-(3,5-dichlorophenyl)-3-(2-propenyl)-2,5-pyrrolidindione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrol-2,5-dione,
3,5-dichloro-N-[cyano[(1-methyl-2-propynyl)-oxy]-methyl]-benzamide,
3-(1,1-dimethylpropyl)-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)-azo]-cyanoacetate,
potassium bicarbonate,
methanetetrathiol-sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzene-sulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran-3'-one,
4-[3,4-dimethoxyphenyl)-3-(4-fluorophenyl)-acryloyl]-morpholine Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:
abamectin, acephate, acetamiprid, acequinocyl, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cyoprene, cyproprothrin, cyfluthrin, cyhalothrin, cyhexatin, cypermethrin, cyromazine, deltamethrin, demeton M, demeton S, demeton-S-methyl, diafenthiuron, diazinon, dichlorvos, dicofol, diflubenzuron, dimethoate, dimethylvinphos, dinetofuran, diofenolan, disulfoton, docusat-sodium, dofenapyn, eflusilanate, emamectin, empenthrin, endosulfan, *Entomopfthora* spp., esfenvalerate, ethiofencarb, ethion, ethiprole, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenthion, fenvalerate, fipronil, fluazinam, fluazuron, flubrocythrinate, flucycloxuron, flucythrinate, flufenoxuron, flumethrin, flupyrazofos, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, indoxacarb, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae*, metharhizium flavoviride, methidathion, methiocarb, methoprene, methomyl, methoxyfenozide, metolcarb, metoxadiazone, mevinphos, milbemectin, milbemycin, monocrotophos, naled, nitenpyram, nithiazine, novaluron, omethoate, oxamyl, oxydemethon M,

*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, spirodiclofen, sulfotep, sulprofos, tau-fluvalinate, tebufenozide, tebufenpyrad, tebupirimiphos, teflubenzuron, tefluthrin, temephos, temivinphos, terbufos, tetrachlorvinphos, tetradifon, theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*,

YI 5302, zeta-cypermethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5] dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N''-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl-[2-(dipropylamino)-2-oxoethyl]-ethylphosphoramidothioate, N-cyanomethyl-4-trifluoromethyl-nicotinamide, 3,5-dichloro-1-(3,3-dichloro-2-propenyloxy)-4-[3-(5-trifluoromethylpyridin-2-yloxy)-propoxy]-benzene.

It is also possible to admix other known active compounds, such as herbicides, or fertilizers and growth regulators, safeners and semichemicals.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the vicinity of the plant, on the surface of parts of plants or in plant tissues.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as by a good stability to alkali on limed substrates.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are understood as meaning plants with novel properties ("traits") which are grown by conventional cultivation, by mutagenesis or by recombinant DNA techniques. These may be cultivars, biotypes or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits which are also particularly emphasized are the increased resistance of plants to fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which cultivars will be developed and/or marketed in the future.

The plants listed can be treated according to the invention in a particularly advantageous manner with the compounds of the formula I or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp.

From the subclass of the Acari (acavids) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Hymenopterons, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example:

building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture or an aliphatic polar organic chemical solvent or solvent mixture is replaced. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl)adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxide, triflumuron, chlothianidin, spinosad, tefluthrin, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as *Serpulidae*, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., in particular fouling by sessile Entomostraka groups, which come under the generic term *Cirripedia* (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:

algicides such as
2-tert-butylamino-4-cyclopropylamino-6-methylthio-1,3, 5-triazine, dichlorophen, diuron, endothal, fentin acetate, isoproturon, methabenzthiazuron, oxyfluorfen, quinoclamine and terbutryn;

fungicides such as
benzo[b]thiophenecarboxylic acid cyclohexylamide S,S-dioxide, dichlofluanid, fluorfolpet, 3-iodo-2-propinyl butyl-carbamate, tolylfluanid and azoles such as azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacarb, Fe-chelate;

or conventional antifouling active compounds such as 4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Omithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free or passive evaporation systems, moth papers, moth bags and moth gels, as granules or dusts, in baits for spreading or in bait stations.

The active compounds according to the invention can also be used as defoliants, desiccants, haulm killers and, especially, as weedkillers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad active spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are: for example ammonium salts and ground natural minerals such as kaolins, clays, talc, chalk, quartz, attapulgite, montmorillonite or diatomaceous earth, and ground synthetic materials such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuiron, anilofos, asulam, atrazine, azafenidin, azimsulfuron, beflubutamid, benazolin (-ethyl), benfuresate, bensulfuron (-methyl), bentazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafensrole, caloxydim, carbetamide, carfentrazone (-ethyl), chlomethoxyfen, chloramben, chloridazon, chlorimuron (-ethyl), chlomitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

Furthermore suitable for the mixtures are known safeners, for example:

AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (-P), mefenpyr (-diethyl), MG-191, oxabetrinil, PPG-1292, R-29148.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The substances according to the invention have potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. gramiriea*

(conidia form: *Drechslera*, syn: *Helminthosporium*);

*Cochliobolus* species, such as, for example, *Cochliobolus sativus*

(conidia form: *Drechslera*, syn: *Helminthosporium*);

*Uromyces* species, such as, for example, *Uromyces appendiculatus;*

*Puccinia* species, such as, for example, *Puccinia recondita;*

*Sclerotinia* species, such as, for example, *Sclerotinia sclerotiorum;*

*Tilletia* species, such as, for example, *Tilletia caries;*

*Ustilago* species, such as, for example, *Ustilago nuda* or *Ustilago avenae;*

*Pellicularia* species, such as, for example, *Pellicularia sasakii;*

*Pyricularia* species, such as, for example, *Pyricularia oryzae;*

*Fusarium* species, such as, for example, *Fusarium culmorum;*

*Botrytis* species, such as, for example, *Botrytis cinerea;*

*Septoria* species, such as, for example, *Septoria nodorum;*

*Leptosphaeria* species, such as, for example, *Leptosphaeria nodorum;*

*Cercospora* species, such as, for example, *Cercospora canescens;*

*Alternaria* species, such as, for example, *Alternaria brassicae*; and

*Pseudocercosporella* species, such as, for example, *Pseudocercosporella herpotrichoides.*

The active compounds according to the invention also have very good fortifying action in plants. Accordingly, they can be used for mobilizing the defences of the plant against attack by undesirable microorganisms.

In the present context, plant-fortifying (resistance-inducing) substances are to be understood as meaning those substances which are capable of stimulating the defence system of plants such that, when the treated plants are subsequently inoculated with undesirable microorganisms, they show substantial resistance against these microorganisms.

In the present case, undesirable microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

At certain concentrations and application rates, the active compounds according to the invention can also be used as herbicides, for influencing plant growth and for controlling animal pests. If appropriate, they can also be used as intermediates and precursors for the synthesis of further active compounds.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (*Basidiomycetes*), and against slime organisms and algae.

Microorganisms of the following genera may be mentioned as examples:

*Alternaria*, such as *Alternaria tenuis,*

*Aspergillus*, such as *Aspergillus niger,*

*Chaetomium*, such as *Chaetomium globosum,*

*Coniophora*, such as *Coniophora puetana,*

*Lentinus*, such as *Lentinus tigrinus,*

*Penicillium*, such as *Penicillium glaucum,*

*Polyporus*, such as *Polyporus versicolor,*

*Aureobasidium*, such as *Aureobasidium pullulans,*

*Sclerophoma*, such as *Sclerophoma pityophila,*

*Trichoderma*, such as *Trichoderma viride,*

*Escherichia*, such as *Escherichia coli,*

*Pseudomonas*, such as *Pseudomonas aeruginosa,* and

*Staphylococcus*, such as *Staphylococcus aureus.*

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following:

Fungicides:

2-phenylphenol; 8-hyroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamide; carvone; quinomethionate; chlobenthiazone; chlorfenazole; chloroneb; chlorothalonil; chlozolinate; clozylacon; cyazofamide; cyflufenamide; cymoxanil; cyproconazole; cyprodinil; cyprofuram; dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamide; fenitropan; fenoxanil; fenpiclonil; fenpropidin; fenpropimorph; ferbam; fluazinam; flubenzimine; fludioxanil; flumetover; flumorph; fluoromide; fluoxastrobin; fluquinconazole; flurprimidol; flusilazole; flusulfamide; flutolanil; flutriafol; folpet; fosetyl-aluminium; fosetyl-sodium; fuberidazole; furalaxyl; furametpyr; furcarbanil; furnecyclox; guazatine; hexachlorobenzene; hexaconazole; hymexazole; imazalil; imibenconazole; iminoctadine triacetate; iminoctadine tris-albesil; iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; proparnocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrine; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)-N-[2-[4-[[3-(4-chlorophenyl)-2-propynyl]oxy]-3-methoxyphenyl]ethyl]-3-methyl-2-[(methylsulphonyl)amino]butanamide; 1-(1-naphthalenyl)-1H-pyrrole-2,5-dione; 2,3,5,6-tetrachloro-4-(methylsulphonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; Actinovate; cis-1-(4-chlorophenyl)-2-(1H-1,2,4-triazol-1-yl)-cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decan-3-amine; sodium tetrathiocarbonate;

and copper salts and copper preparations, such as Bordeaux mixture; copper hydroxide; copper naphthenate; copper oxychloride; copper sulphate; cufraneb; cuprous oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amidoflumet, aminocarb, amitraz, avermectin, AZ-60541, azadirachtin, azamethiphos, azinphos-methyl, azinphos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, bendiocarb, benfuracarb, bensultap, benzoximate, beta-cyfluthrin, beta-cypermethrin, bifenazate, bifenthrin, binapacryl, bioallethrin, bioallethrin-S-cyclopentyl-isomer, bioethanomethrin, biopermethrin, bioresmethrin, bistrifluron, BPMC, brofenprox, bromophos-ethyl, bromopropylate, bromfenvinfos (-methyl), BTG-504, BTG-505, bufencarb, buprofezin, butathiofos, butocarboxim, butoxy-carboxim, butylpyridaben, cadusafos, camphechlor, carbaryl, carbofuran, carbophenothion, carbosulfan, cartap, CGA-50439, quinomethionate, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (ethyl), chlovaporthrin, chromafenozide, cis-cypermethrin, cis-resmethrin, cis-permethrin, clocythrin, cloethocarb, clofentezine, clothianidine, clothiazoben, codlemone, coumaphos, cyanofenphos, cyanophos, cycloprene, cycloprothrin, cydia pomanella, cyfluthrin, cyhalothrin, cyhexatin, cypermethrin, cyphenothrin (1R-trans-isomer), cyromazine, DDT, deltamethrin, demeton-S-methyl, demeton-S-methylsulphon, diafenthiuron, dialifos, diazinon, dichlofenthion, dichlorvos, dicofol, dicrotophos, dicyclanil, diflubenzuron, dimethoate, dimethylvinphos, dinobuton, dinocap, dinetefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamide, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, fonnetanate, formothion, fosmethilan, fosthiazate, fubfenprox (fluproxyfen), furathiocarb, Gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methanacrifos, methamidophos, *Metharhizium anisopliae, Metharhizium flavoviride*, methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus*, parathion-methyl, parathion (-ethyl), permethrin (cis-, trans-), petroleum, PH-6045, phenothrin. (IR-trans isomer), phenthoate, phorate, phosalone, phosmet, phosphamidon, phosphocarb, phoxim, piperonyl butoxide, pirimicarb, pirimiphos-methyl, pirimiphos-ethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RH-12457, RH-15525, S-421, S-1833, salithion, sebufos, S1-0009, silafluofen, spinosad, spirodiclofen, spiromesifen, sulfluramide, sulfotep, sulprofos, S21-121, tau-fluvalinate, tebufenozide, tebufenpyrad, tebupirimfos, teflubenzuron, tefluthrin, temephos, temivinphos, terbarn, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*, WL-108477, WL-40027,

YI-5201, YI-5301, YI-5302,

XMC, xylylcarb,

ZA-3274, zeta-cypermethrin, zolaprofos, ZXI-8901, the compound 3-methylphenyl propylcarbamate (Tsumacide Z), the compound 3-(5-chloro-3-pyridinyl)-8-(2,2,2-trifluoroethyl)-8-azabicyclo[3.2.1]-octane-3-carbonitrile (CAS-Reg. No. 185982-80-3) and the corresponding 3-endo isomer (CAS-Reg. No. 185984-60-5) (cf. WO-96/37494, WO-98/25923), and preparations comprising insecticidally active plant extracts, nematodes, fungi or viruses.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes*,

*Microsporon* species such as *Microsporon canis* and *audouinii*. The list of these fungi by no means limits the mycotic spectrum covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low-volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

The preparation and the use of the active compounds according to the invention are illustrated by the examples below.

PREPARATION EXAMPLES

Example I-a-1

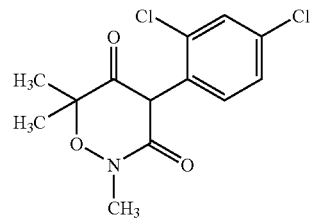

0.79 g (20 mmol) of 60% sodium hydride is initially charged in anhydrous DMF. At room temperature, 3.13 g (9 mmol) of the compound of Example II-1 in a little DMF are added dropwise. The mixture is stirred at room temperature overnight.

The reaction mixture is poured into ice-water, acidified with conc. hydrochloric acid and extracted with dichloromethane, and the organic phase is separated off and concentrated. The residue is purified by silica gel column chromatography (dichloromethane/methanol, 30:1).

Yield: 0.95 g (34% of theory), m.p. 69° C.

Analogously to Example I-a-1 and in accordance with the general statements, the following compounds of the formula (I-a) are obtained:

diacetate of the title compound which is immediately hydrolysed.

Yield: 0.534 g (43.9% of theory)

0.17 g (0.46 mmol) of the diacetate and 0.04 g (1 mmol) of NaOH in 1 ml of ethanol are stirred at room temperature overnight. The mixture is poured into water and extracted twice with $CH_2Cl_2$ and the extract is dried over $MgSO_4$ and concentrated. The residue crystallizes partially and is triturated with hexane. The resulting solid is filtered off.

Yield: 13 mg (10% of theory)

Melting point: 127° C.

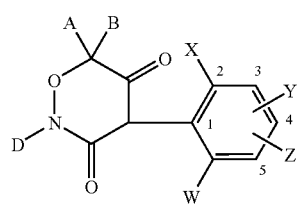

(I-a)

| Ex. No. | W | X | Y | Z | D | A | B | m.p. ° C. |
|---|---|---|---|---|---|---|---|---|
| I-a-2 | H | $CH_3$ | 4-$OCH_3$ | 5-$CH_3$ | $CH_3$ | $CH_3$ | $CH_3$ | 137–138 |
| I-a-3 | H | $CH_3$ | 4-$CH_3$ | H | $CH_3$ | $CH_3$ | $CH_3$ | 110 |
| I-a-4 | Cl | Cl | 4-$CF_3$ | H | $CH_3$ | $CH_3$ | $CH_3$ | 163 |
| I-a-5 | H | $CH_3$ | 4-$CH_3$ | 5-$CH_3$ | $CH_3$ | $CH_3$ | $CH_3$ | 104 |
| I-a-6 | H | $CH_3$ | H | 5-(4-Cl—$C_6H_4$) | $CH_3$ | —$(CH_2)_3$— | | 162 |
| I-a-7 | H | $CH_3$ | H | 5-(4-Cl—$C_6H_4$) | $CH_3$ | $CH_3$ | $CH_3$ | 153 |
| I-a-8 | $CH_3$ | $CH_3$ | 4-$CH_3$ | H | $CH_3$ | $CH_3$ | $CH_3$ | 110 |
| I-a-9 | $CH_3$ | $CH_3$ | 4-Br | H | $CH_3$ | $CH_3$ | $CH_3$ | 181 |
| I-a-10 | H | Cl | H | 5-(4-Cl—$C_6H_4$) | $CH_3$ | —$(CH_2)_3$— | | 160 |
| I-a-11 | $CH_3$ | $CH_3$ | 4-$CH_3$ | 3-$CH_3$ | $CH_3$ | $CH_3$ | $CH_3$ | 161 |
| I-a-12 | H | Cl | H | 5-(4-Cl—$C_6H_4$) | $CH_3$ | $CH_3$ | $CH_3$ | 143.5 |
| I-a-13 | $CH_3$ | $CH_3$ | 4-$CH_3$ | H | $CH_3$ | —$(CH_2)_4$— | | 163 |
| I-a-14 | $C_2H_5$ | $CH_3$ | 4-Br | H | $CH_3$ | $CH_3$ | $CH_3$ | 188 |
| I-a-15 | H | $CH_3$ | 4-Br | 5-$CH_3$ | $CH_3$ | $CH_3$ | $CH_3$ | 112 |
| I-a-16 | H | Br | 4-$CH_3$ | 5-$CH_3$ | $CH_3$ | $CH_3$ | $CH_3$ | 117 |

Example I-a-17

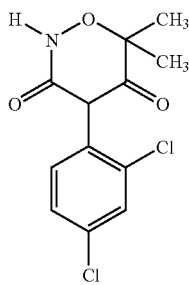

1.0 g (3.27 mmol) of the compound of Example II-10 and a spatula tip of anhydrous sodium acetate in 10 ml of acetic anhydride are heated under reflux overnight. 20 ml of water are added, the mixture is extracted twice with $CH_2Cl_2$ and the extract is washed with $NaHCO_3$ solution, dried over $MgSO_4$ and concentrated. The residue is triturated with cyclohexane and the resulting solid is filtered off and discarded. The filtrate is concentrated. This gives the N,O-

Example I-b-1

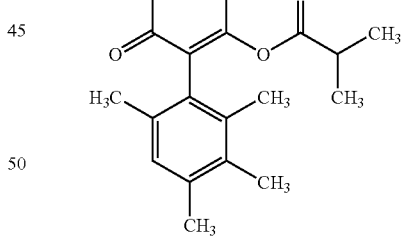

0.32 g (1,09 mmol) of the compound of Example I-a-11 is initially charged in 5 ml of $CH_2Cl_2$, and 0.11 g (1.09 mmol) of triethylamine is added. 0.12 g (1.09 mmol) of isobutyryl chloride is added. The mixture is stirred under reflux overnight and then washed with 1N hydrochloric acid. The organic phase is dried and the solvent is distilled off. The residue is chromatographed on silica gel using cyclohexane/ethyl acetate 10:3.

Yield: 0.297 g (75.8% of theory)

Melting point: 53° C.

The following compounds of the formula (I-b) are obtained analogously to Example 1-b-1 and in accordance with the general statements:

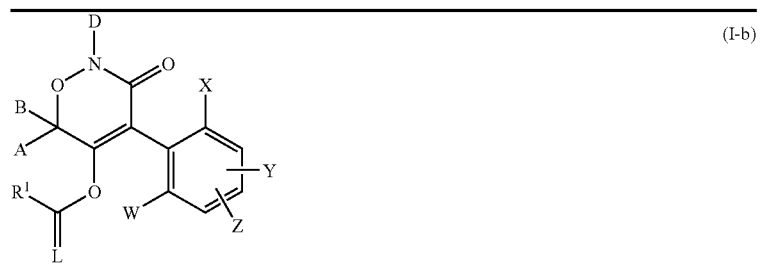

| Ex. No. | W | X | Z | Y | D | A | B | L | R[1] | m.p. ° C. |
|---|---|---|---|---|---|---|---|---|---|---|
| I-b-2 | H | CH$_3$ | 5-(4-Cl—C$_6$H$_4$) | H | CH$_3$ | CH$_3$ | CH$_3$ | O | (CH$_3$)$_2$CH | 93.5 |

Example I-c-1

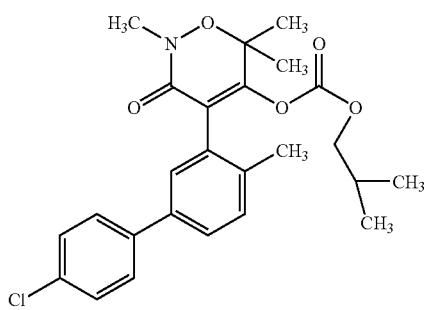

0.3 g (0.84 mmol) of the compound of Example I-a-7 initially charged in 5 ml of CH$_2$Cl$_2$, and 0.08 g (0.84 mmol) of triethylamine is added. 0.11 g (0.84 mmol) of isobutyl chloroformate in anhydrous CH$_2$Cl$_2$ is added dropwise at room temperature. The mixture is stirred under reflux. After the reaction has ended, the mixture is washed with diluted hydrochloric acid, the organic phase is dried and the solvent is distilled off.

Yield: 0.28 g (74% of theory)

The following compounds of the formula (I-c) are obtained analogously to Example I-c-1 and in accordance with the general statements Example II-1

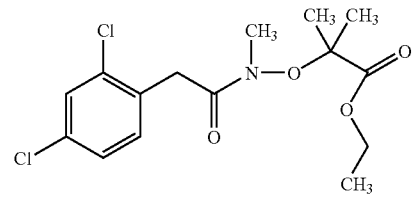

4 g (17 mmol) of the compound of Example XIX-1 and 4 g (20.5 mmol) of ethyl bromoisobutyrate are initially charged in anhydrous acetone, and 2.8 g (20.5 mmol) of potassium carbonate are added. The mixture is stirred at 40° C. for 8 h. The mixture is filtered and the filtrate is concentrated. The residue is taken up in dichloromethane and the organic phase is washed with water and brine, dried and concentrated.

Yield: 4.295 g (72% of theory).

$^1$H-NMR (400 MHz, CDCl$_3$): δ (ppm)=1.32; t; 3H; J=6.7 Hz, (CH$_2$—<u>CH$_3$</u>) 1.58; s; 6H; (2×<u>CH$_3$</u>); 3.22; s; 3H; (N—<u>CH$_3$</u>); 3.91; s; 2H; (—CH$_2$—); 4.25; q; J=6.7 Hz; 2H (O—CH$_2$—); 7.2; m; 2H (arom. H); 7.39; m; 1H (arom. H).

| Ex. No. | W | X | Z | Y | D | A | B | L | M | R[2] | m.p. ° C. |
|---|---|---|---|---|---|---|---|---|---|---|---|
| I-c-2 | CH$_3$ | CH$_3$ | 3-CH$_3$ | 4-CH$_3$ | CH$_3$ | CH$_3$ | CH$_3$ | O | O | (CH$_3$)$_2$CH—CH$_2$ | oil |
| I-c-3 | H | CH$_3$ | 5-(4-Cl—C$_6$H$_4$) | H | CH$_3$ | CH$_3$ | CH$_3$ | O | O | C$_2$H$_5$— | oil |
| I-c-4 | H | CH$_3$ | 5-(4-Cl—C$_6$H$_4$) | H | CH$_3$ | —(CH$_2$)$_3$— | | O | O | C$_2$H$_5$— | oil |
| I-c-5 | H | Cl | 5-(4-Cl—C$_6$H$_4$) | H | CH$_3$ | CH$_3$ | CH$_3$ | O | O | (CH$_3$)$_2$CH—CH$_2$ | oil |
| I-c-6 | H | Cl | 5-(4-Cl—C$_6$H$_4$) | H | CH$_3$ | —(CH$_2$)$_3$— | | O | O | —(CH$_2$)$_3$— | oil |
| I-c-7 | H | Cl | 5-(4-Cl—C$_6$H$_4$) | H | CH$_3$ | —(CH$_2$)$_3$— | | O | O | (CH$_3$)$_2$CH—CH$_2$ | oil |

Example II-2

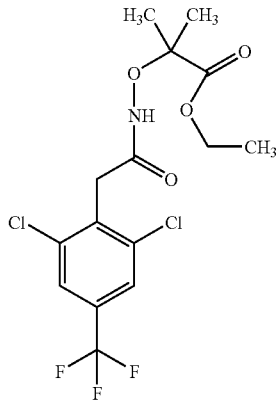

0.74 g (5 mmol) of the compound of Example XIII-1 and 0.44 g (5.5 mmol) of pyridine are together initially charged in anhydrous dichloromethane, at 0° C. 1.6 g (5.5 mmol) of 2,6-dichloro-4-trifluoromethylphenylacetyl chloride are added. The reaction mixture is stirred at room temperature overnight and then poured into water and washed with dilute sulphuric acid, and the organic phase is separated off and concentrated. The residue is triturated with hexane and the solid is filtered off with suction.

Yield: 1.62 g (80% of theory), m.p. 152° C.

Example II-3

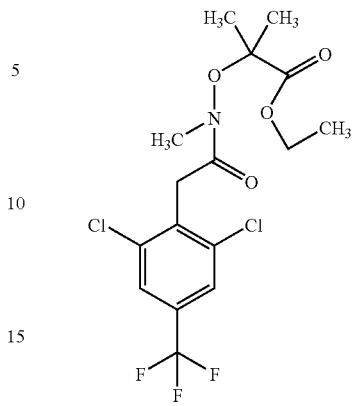

At room temperature, 0.1 g of sodium hydride is initially charged in 5 ml of anhydrous DMF in a stirred three-necked flask fitted with high-performance condenser and thermometer. 0.89 g (1.99 mmol) of the compound of Example II-2, dissolved in 10 ml of anhydrous DMF, is added dropwise. The mixture is stirred for 10 min. 0.31 g (2.19 mmol) of methyl iodide is then added dropwise. The mixture is stirred at room temperature overnight. The reaction solution is poured into 50 ml of ice-water and extracted with 20 ml of dichloromethane, and the organic phase is dried and concentrated.

Yield: 0.78 g (94% of theory).

$^1$H-NMR (CDCl$_3$); δ (ppm)=1.35; t; J=7 Hz (OCH$_2$—CH$_3$); 1.63; s; 6H; (2×—CH$_3$), 3.23; s; 3H; (N—CH$_3$); 4.22; s; 2H; (—CH$_2$—); 4.28; q; J=7 Hz; 2H (O—$\underline{CH_2}$—CH$_3$); 7.58; s; 2H (arom. H).

Analogously to Examples II-1 to II-3 and in accordance with the general statements on the preparation, the following compounds of the formula (II) are obtained:

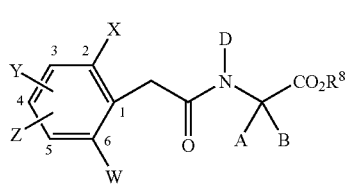

(II)

| Ex. No. | W | X | Y | Z | D | A | B | m.p. ° C. |
|---|---|---|---|---|---|---|---|---|
| II-4 | CH$_3$ | CH$_3$ | 4-CH$_3$ | H | CH$_3$ | CH$_3$ | CH$_3$ | oil |
| II-5 | H | CH$_3$ | H | 5-(4-Cl—C$_6$H$_4$) | CH$_3$ | CH$_3$ | CH$_3$ | oil |
| II-6 | H | CH$_3$ | 4-OCH$_3$ | 5-CH$_3$ | CH$_3$ | CH$_3$ | CH$_3$ | oil |
| II-7 | H | CH$_3$ | 4-CH$_3$ | H | H | CH$_3$ | CH$_3$ | 76 |
| II-8 | CH$_3$ | CH$_3$ | 4-Br | H | H | CH$_3$ | CH$_3$ | 147 |
| II-9 | H | CH$_3$ | H | 5-(4-Cl—C$_6$H$_4$) | H | CH$_3$ | CH$_3$ | 78 |
| II-10 | H | Cl | 4-Cl | H | H | CH$_3$ | CH$_3$ | 94 |
| II-11 | H | CH$_3$ | 4-CH$_3$ | 5-CH$_3$ | H | CH$_3$ | CH$_3$ | 110 |
| II-12 | H | CH$_3$ | 4-CH$_3$ | H | H | i-C$_3$H$_7$ | H | 71 |
| II-13 | H | CH$_3$ | 4-CH$_3$ | H | CH$_3$ | CH$_3$ | CH$_3$ | oil |
| II-14 | H | CH$_3$ | 4-CH$_3$ | 5-CH$_3$ | CH$_3$ | CH$_3$ | CH$_3$ | oil |
| II-15 | CH$_3$ | CH$_3$ | 4-Br | H | CH$_3$ | CH$_3$ | CH$_3$ | oil |
| II-16 | H | CH$_3$ | 4-CH$_3$ | H | CH$_2$—O—C$_2$H$_5$ | CH$_3$ | CH$_3$ | oil |
| II-17 | CH$_3$ | CH$_3$ | 4-CH$_3$ | H | H | —(CH$_2$)$_4$— | | 95 |
| II-18 | CH$_3$ | CH$_3$ | 4-CH$_3$ | H | CH$_3$ | —(CH$_2$)$_4$— | | oil |
| II-19 | CH$_3$ | CH$_3$ | 4-CH$_3$ | H | H | —(CH$_2$)$_3$— | | 115 |
| II-20 | CH$_3$ | CH$_3$ | 4-CH$_3$ | H | CH$_3$ | —(CH$_2$)$_3$— | | oil |
| II-21 | CH$_3$ | CH$_3$ | 4-Cl | H | H | CH$_3$ | CH$_3$ | 116 |
| II-22 | CH$_3$ | CH$_3$ | 4-Cl | H | CH$_3$ | CH$_3$ | CH$_3$ | oil |

-continued (II)

[Structure of formula II: substituted phenylacetamide with CO2R8 group]

| Ex. No. | W | X | Y | Z | D | A | B | m.p. ° C. |
|---|---|---|---|---|---|---|---|---|
| II-23 | C$_2$H$_5$ | CH$_3$ | 4-Br | H | H | CH$_3$ | CH$_3$ | 119.5 |
| II-24 | C$_2$H$_5$ | CH$_3$ | 4-Br | H | CH$_3$ | CH$_3$ | CH$_3$ | oil |
| II-25 | H | Br | 4-CH$_3$ | 5-CH$_3$ | H | CH$_3$ | CH$_3$ | 120 |
| II-26 | H | Br | 4-CH$_3$ | 5-CH$_3$ | CH$_3$ | CH$_3$ | CH$_3$ | oil |
| II-27 | H | CH$_3$ | 4-Br | 5-CH$_3$ | H | CH$_3$ | CH$_3$ | 127 |
| II-28 | H | CH$_3$ | 4-Br | 5-CH$_3$ | CH$_3$ | CH$_3$ | CH$_3$ | oil |
| II-29 | CH$_3$ | CH$_3$ | 4-Br | 3-CH$_3$ | H | CH$_3$ | CH$_3$ | 150 |
| II-30 | CH$_3$ | CH$_3$ | 4-Br | 3-CH$_3$ | CH$_3$ | CH$_3$ | CH$_3$ | oil |
| II-31 | H | CH$_3$ | H | 5-(4-Cl—C$_6$H$_4$) | H | —(CH$_2$)$_3$— | | 133 |
| II-32 | H | CH$_3$ | H | 5-(4-Cl—C$_6$H$_4$) | CH$_3$ | —(CH$_2$)$_3$— | | oil |
| II-33 | H | Cl | H | 5-(4-Cl—C$_6$H$_4$) | H | —(CH$_2$)$_3$— | | 120 |
| II-34 | H | Cl | H | 5-(4-Cl—C$_6$H$_4$) | CH$_3$ | —(CH$_2$)$_3$— | | oil |

Example XIII-1

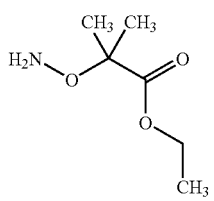

141 g (511 mmol) of the compound of Example XVII-1 are initially charged in 1000 ml of methanol and 1000 ml of dichloromethane. 65 g of hydrazine hydrate are added. The mixture is stirred under reflux for 3 h. The mixture is cooled and the solid is filtered off with suction and washed with dichloromethane. 5 l of 5% strength Na$_2$CO$_3$ solution are added, and the mixture is extracted 5 times with dichloromethane. The organic phase is dried and concentrated. The residue is distilled under high vacuum.

Yield: 64 g (85% of theory);

Boiling point: 40° C./0.55 mbar

Analogously to Example XIII-1 and in accordance with the general statements on the preparation, the following compounds of the formula XIII are obtained:

(XIII)

[Structure of formula XIII: H$_2$N—O—C(A)(B)—CO$_2$R$^8$]

| Ex. No. | A | B | R$^8$ | b.p. ° C./mbar |
|---|---|---|---|---|
| XIII-2 | —(CH$_2$)$_4$— | | C$_2$H$_5$ | 48–55/52 |
| XIII-3 | i-C$_3$H$_7$ | H | C$_2$H$_5$ | 114/60 |
| XIII-4 | —(CH$_2$)$_3$— | | C$_2$H$_5$ | |

Example XVIII-1

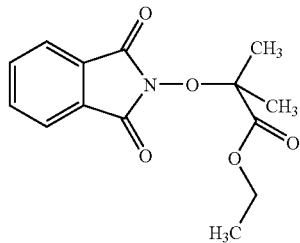

100 g of N-hydroxphthalimide and 119 g of bromoisobutyrate are together initially charged in 1000 ml of anhydrous DMF in a stirred three-necked flask fitted with high-performance condenser and thermometer. 62 g of triethylamine are added, and the mixture is stirred at 60° C. for 28 h. The reaction mixture is poured into 500 ml of water and extracted 4 times with 150 ml of MTBE, the organic phase is dried and concentrated and the residue is triturated with hexane. The solid is filtered off with suction.

Yield: 141 g (83% of theory); m.p. 80° C.

The following compounds of the formula (XVII) are obtained analogously to Example XVII-1 and in accordance with the general statements on the preparation:

(XVII)

[Structure of formula XVII: phthalimide-N—O—C(A)(B)—CO$_2$R$^8$]

| Ex. No. | A | B | R$^8$ | m.p. ° C. |
|---|---|---|---|---|
| XVII-2 | —(CH$_2$)$_4$— | | C$_2$H$_5$ | 83 |
| XVII-3 | i-C$_3$H$_7$ | H | C$_2$H$_5$ | oil |
| XVII-4 | —(CH$_2$)$_3$— | | C$_2$H$_5$ | 109 |

Example XIX-1

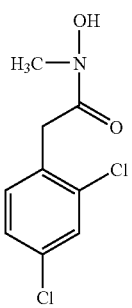

At room temperature, 5.3 g (23 mol) of 2,4-dichlorophenylacetyl chloride and 1.98 g (23 mol) of N-methylhydroxylamine hydrochloride are initially charged in anhydrous dichloromethane. 4.8 g of triethylamine are slowly added dropwise. The mixture is stirred at room temperature overnight and then washed with dilute hydrochloric acid and with NaHCO₃ solution. The organic phase is dried and concentrated and the solid is taken up in MTBE and washed with dilute hydrochloric acid. The organic phase is dried and concentrated.

Yield: 4.12 g (74% of theory); m.p. 103° C.

Analogously to Example XIX-1 and in accordance with the general statements of the preparation, the following examples of the formula (XIX) are obtained:

(XIX)

| Ex. No. | W | X | Y | Z | D | m.p. ° C. |
|---|---|---|---|---|---|---|
| XIX-2 | CH₃ | CH₃ | 4-CH₃ | H | CH₃ | 130 |
| XIX-3 | H | CH₃ | H | 5-(4-Cl—C₆—H₄) | CH₃ | oil |
| XIX-4 | H | CH₃ | 4-OCH₃ | 5-CH₃ | CH₃ | 115 |

Example A

*Myzus* Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the peach aphid (*Myzus persicae*) are treated by being dipped into the preparation of active compound of the desired concentration.

After the desired period of time, the kill in % is determined. 100% means that all aphids have been killed; 0% means that none of the aphids has been killed.

In this test, for example, the following compound of the preparation examples shows good activity:

TABLE A

| | Plant-damaging insects Myzus test | |
|---|---|---|
| Active compounds | Concentration of active compound in ppm | Kill rate in % after 6$^d$ |
| Example I-a-7 | 500 | 90 |

Example B

*Phaedon* Larvae Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae has been killed.

In this test, for example, the following compounds of the Preparation Examples show good activity:

TABLE B

| | Plant-damaging insects Phaedon larvae test | |
|---|---|---|
| Active compounds | Concentration of active compound in ppm | Kill rate in % after 7$^d$ |
| Example I-a-7 | 500 | 100 |
| Example I-c-1 | 500 | 100 |

Example C

*Spodoptera frugiperda* Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the armyworm (*Spodoptera frugiperda*) while the leaves are still moist.

After the desired period of time, the kill in % is determined. 100% means that all caterpillars have been killed; 0% means that none of the caterpillars has been killed.

In this test, for example, the following compound of the Preparation Examples shows good activity:

TABLE C

| | Plant-damaging insects Spodoptera frugiperda test | |
|---|---|---|
| Active compounds | Concentration of active compound in ppm | Kill rate in % after 7$^d$ |
| Example I-c-1 | 500 | 100 |

Example D

*Tetranychus* Test (OP-Resistant/dip Treatment)
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the effect in % is determined. 100% means that all spider mites have been killed; 0% means that none of the spider mites has been killed.

In this test, for example, the following compounds of the Preparation Examples show good activity:

TABLE D

| | Plant-damaging mites Tetranychus test (OP-resistant/dip treatment) | |
|---|---|---|
| Active compounds | Concentration of active compound in ppm | Kill rate in % after 7$^d$ |
| Example I-a-7 | 100 | 100 |
| Example I-c-1 | 100 | 98 |

Example E

Critical Concentration Test/Soil Insects—Treatment of Transgenic Plants

Test Insect: *Diabrotica balteata*—Larvae in Soil
Solvent: 7 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial, only the amount by weight of active compounds per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trade mark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

Example F

*Heliothis virescens* Test—Treatment of Transgenic Plants
Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soybean shoots (*Glycine max*) of the cultivar Roundup Ready (trade mark of Monsanto Comp. USA) are treated by being dipped into the preparation of active compound of the desired concentration and are populated with the tobacco budworm *Heliothis virescens* while the leaves are still moist.

After the desired period of time, the kill of the insects is determined.

What is claimed is:

1. A compound represented by formulas (I-A) and/or (1-B)

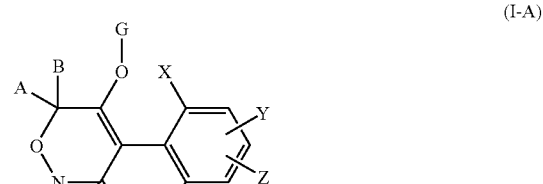

(I-A)

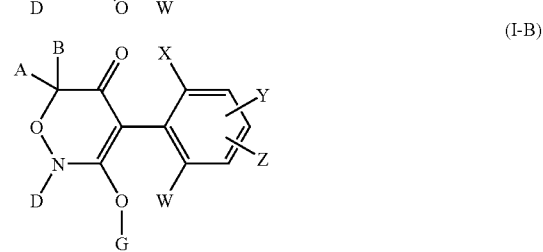

(I-B)

in which
(a) W represents hydrogen, halogen, $C_1$–$C_6$-alkyl, or $C_1$–$C_6$-alkoxy, X represents halogen, $C_1$–$C_6$-alkyl, $C_1$–$C_6$-alkoxy, $C_1$–$C_4$-haloalkyl, $C_1$–$C_4$-haloalkoxy, or cyano, Y in the 4-position represents hydrogen, $C_1$–$C_6$-alkoxy, halogen, cyano, or $C_1$–$C_4$-haloalkyl, and Z in the 3- or 5-position represents hydrogen or $C_1$–$C_6$-alkyl, or (b) W represents hydrogen, halogen, or $C_1$–$C_6$-alkyl, X represents halogen, $C_1$–$C_6$-alkyl, $C_1$–$C_6$-alkoxy, $C_1$–$C_4$-haloalkyl, $C_1$–$C_4$-haloalkoxy, or cyano, Y in the 4-position represents a radical

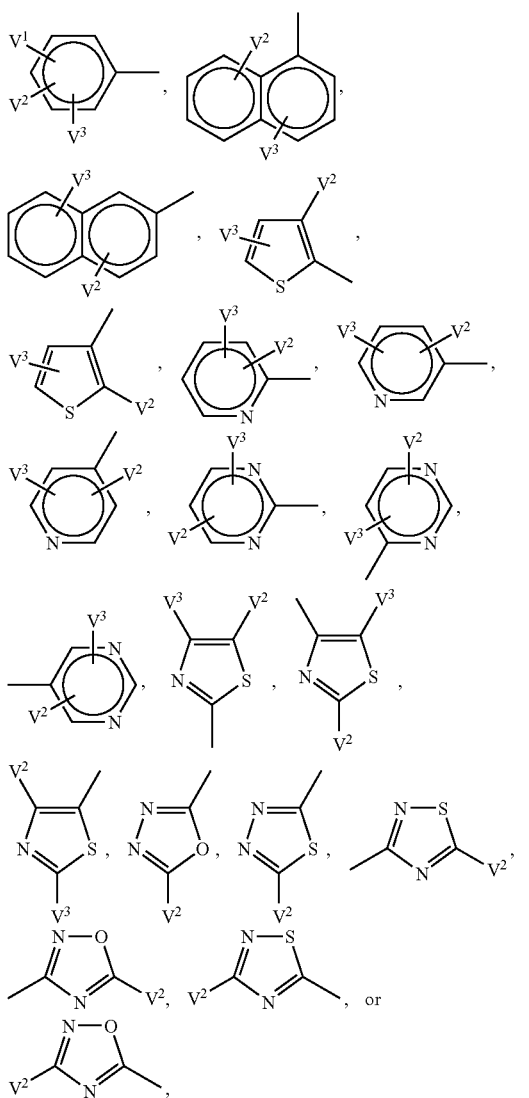

in which
- $V^1$ represents hydrogen, halogen, $C_1$–$C_{12}$-alkyl, $C_1$–$C_6$-alkoxy, $C_1$–$C_6$-alkylthio, $C_1$–$C_6$-alkylsulphinyl, $C_1$–$C_6$-alkylsulphonyl, $C_1$–$C_4$-haloalkyl, $C_1$–$C_4$-haloalkoxy, nitro, or cyano or represents phenyl, phenoxy, phenoxy-$C_1$–$C_4$-alkyl, phenyl-$C_1$–$C_4$-alkoxy, phenylthio-$C_1$–$C_4$-alkyl, or phenyl-$C_1$–$C_4$-alkylthio, each of which is optionally mono- or polysubstituted by halogen, $C_1$–$C_6$-alkyl, $C_1$–$C_6$-alkoxy, $C_1$–$C_4$-haloalkyl, $C_1$–$C_4$-haloalkoxy, nitro, or cyano, and
- $V^2$ and $V^3$ independently of one another represent hydrogen, halogen, $C_1$–$C_6$alkyl, $C_1$–$C_6$-alkoxy, $C_1$–$C_4$-haloalkyl, or $C_1$–$C_4$-haloalkoxy, or
- $V^1$ and $V^2$ together represent $C_3$–$C_4$-alkanediyl that is optionally substituted by halogen and/or $C_1$–$C_2$-alkyl and that is optionally interrupted by one or two oxygen atoms, and
- Z represents hydrogen, or (c) W represents hydrogen, halogen, or $C_1$–$C_6$-alkyl, X represents halogen, $C_1$–$C_6$-alkyl, $C_1$–$C_6$-alkoxy, $C_1$–$C_4$-haloalkyl, $C_1$–$C_4$-haloalkoxy, or cyano, Y in the 4-position represents hydrogen, $C_1$–$C_6$-alkyl, or halogen, and Z in the 5-position represents a radical

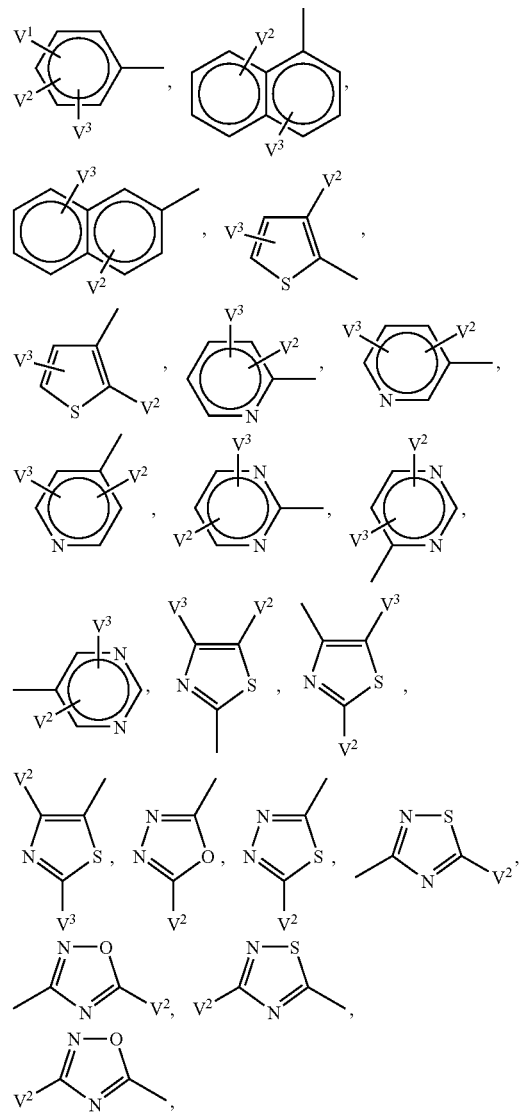

in which
- $V^1$ represents hydrogen, halogen, $C_1$–$C_{12}$-alkyl, $C_1$–$C_6$-alkoxy, $C_1$–$C_6$-alkylthio, $C_1$–$C_6$-alkylsulphinyl, $C_1$–$C_6$-alkylsulphonyl, $C_1$–$C_4$-haloalkyl, $C_1$–$C_4$-haloalkoxy, nitro, or cyano; or represents phenyl, phenoxy, phenoxy-$C_1$–$C_4$-alkyl, phenyl-$C_1$–$C_4$-alkoxy, phenylthio-$C_1$–$C_4$-alkyl, or phenyl-$C_1$–$C_4$-alkylthio, each of which is optionally mono- or polysubstituted by halogen, $C_1$–$C_6$-alkyl, $C_1$–$C_6$-alkoxy, $C_1$–$C_4$-haloalkyl, $C_1$–$C_4$-haloalkoxy, nitro, or cyano, and
- $V^2$ and $V^3$ independently of one another represent hydrogen, halogen, $C_1$–$C_6$-alkyl, $C_1$–$C_6$-alkoxy, $C_1$–$C_4$-haloalkyl, or $C_1$–$C_4$-haloalkoxy, or V$^1$ and V$^2$ together represent C$_3$–C$_4$-alkanediyl that is optionally substituted by halogen and/or C$_1$–C$_2$-alkyl and that is optionally interrupted by one or two oxygen atoms, or
(d) W represents hydrogen, methyl, propyl, isopropyl or halogen,
X represents halogen, C$_1$–C$_6$-alkyl, C$_1$–C$_6$-alkoxy, C$_1$–C$_4$-haloalkyl, C$_1$–C$_4$-haloalkoxy, or cyano,
Y in the 4-position represents hydrogen, halogen, C$_1$–C$_6$-alkyl, C$_1$–C$_4$-haloalkyl, cyano, or C$_1$–C$_4$-haloalkoxy, and
Z in the 3- or 5-position represents hydrogen, halogen, or C$_1$–C$_6$-alkyl, and
A represents hydrogen; represents optionally halogen-substituted C$_1$–C$_{12}$-alkyl, C$_3$–C$_8$-alkenyl, C$_1$–C$_{10}$-alkoxy-C$_1$–C$_8$-alkyl, poly-C$_1$–C$_8$-alkoxy-C$_1$–C$_8$-alkyl, or C$_1$–C$_{10}$-alkylthio-C$_1$–C$_6$-alkyl; or represents optionally halogen-, C$_1$–C$_6$alkyl-, or C$_1$–C$_6$-alkoxy-substituted C$_3$–C$_8$-cycloalkyl in which one or two ring members that are not directly adjacent are optionally replaced by oxygen and/or sulphur,
B represents hydrogen, C$_1$–C$_{12}$-alkyl, or C$_1$–C$_8$-alkoxy-C$_1$–C$_6$-alkyl, or
A, B, and the carbon atom to which they are attached represent saturated C$_3$–C$_{10}$-cycloalkyl or unsaturated C$_5$–C$_{10}$-cycloalkyl in which one ring member is optionally replaced by oxygen or sulphur and that are optionally mono- or disubstituted by C$_1$–C$_8$-alkyl, C$_3$–C$_{10}$-cycloalkyl, C$_1$–C$_8$-haloalkyl, C$_1$–C$_8$-alkoxy, C$_1$–C$_8$-alkylthio, halogen, or phenyl,
D represents hydrogen; represents optionally halogen-substituted C$_1$–C$_{12}$-alkyl, C$_3$–C$_8$-alkenyl, C$_1$–C$_{10}$-alkoxy-C$_2$–C$_8$-alkyl, poly-C$_1$–C$_8$-alkoxy-C$_2$–C$_8$-alkyl, C$_1$–C$_{10}$-alkylthio-C$_2$–C$_8$-alkyl, optionally halogen-, C$_1$–C$_4$-alkyl-, C$_1$–C$_4$-alkoxy-, or C$_1$–C$_4$-haloalkyl-substituted C$_3$–C$_8$-cycloalkyl in which one ring member is optionally replaced by oxygen or sulphur, and
G represents hydrogen (a) or represents one of the groups (b)
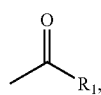

(c)
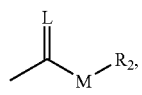

(d)
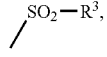

(e)

(f)
E or (g)
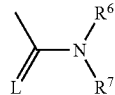

in which
E represents a metal ion equivalent or an ammonium ion,

L represents oxygen or sulphur,
M represents oxygen or sulphur,
R$^1$ represents optionally halogen-substituted C$_1$–C$_{20}$-alkyl, C$_2$–C$_{20}$-alkenyl, C$_1$–C$_8$-alkoxy-C$_1$–C$_8$-alkyl, C$_1$–C$_8$-alkylthio-C$_1$–C$_8$-alkyl, poly-C$_1$–C$_8$-alkoxy-C$_1$–C$_8$-alkyl or optionally halogen-, C$_1$–C$_6$-alkyl-, or C$_1$–C$_6$-alkoxy-substituted C$_3$–C$_8$-cycloalkyl in which one or more ring members that are not directly adjacent are optionally replaced by oxygen and/or sulphur; represents optionally halogen-, cyano-, nitro-, C$_1$–C$_6$-alkyl-, C$_1$–C$_6$-alkoxy-, C$_1$–C$_6$-haloalkyl-, C$_1$–C$_6$-haloalkoxy-, C$_1$–C$_6$-alkylthio-, or C$_1$–C$_6$-alkylsulfonyl-substituted phenyl; represents optionally halogen-, nitro-, cyano-, C$_1$–C$_6$-alkyl-, C$_1$–C$_6$-alkoxy-, C$_1$–C$_6$-haloalkyl-, or C$_1$–C$_6$-haloalkoxy-substituted phenyl-C$_1$–C$_6$-alkyl; represents optionally halogen- or C$_1$–C$_6$-alkyl-substituted 5- or 6-membered hetaryl; represents optionally halogen- or C$_1$–C$_6$-alkyl-substituted phenoxy-C$_1$–C$_6$-alkyl; or represents optionally halogen-, amino-, or C$_1$–C$_6$-alkyl-substituted 5- or 6-membered hetaryloxy-C$_1$–C$_6$-alkyl,
R$^2$ represents optionally halogen-substituted C$_1$–C$_{20}$-alkyl, C$_2$–C$_{20}$-alkenyl, C$_1$–C$_8$-alkoxy-C$_2$–C$_8$-alkyl, or poly-C$_1$–C$_8$-alkoxy-C$_2$–C$_8$-alkyl; represents optionally halogen-, C$_1$–C$_6$-alkyl-, or C$_1$–C$_6$-alkoxy-substituted C$_3$–C$_8$-cycloalkyl; or represents optionally halogen-, cyano-, nitro-, C$_1$–C$_6$-alkyl-, C$_1$–C$_6$-alkoxy-, C$_1$–C$_6$-haloalkyl-, or C$_1$–C$_6$-haloalkoxy-substituted phenyl or benzyl,
R$^3$ represents optionally halogen-substituted C$_1$–C$_8$-alkyl; or represents optionally halogen-, C$_1$–C$_6$-alkyl-, C$_1$–C$_6$-alkoxy-, C$_1$–C$_4$-haloalkyl-, C$_1$–C$_4$-haloalkoxy-, cyano-, or nitro-substituted phenyl or benzyl,
R$^4$ and R$^5$ independently of one another represent optionally halogen-substituted C$_1$–C$_8$-alkyl, C$_1$–C$_8$-alkoxy, C$_1$–C$_8$-alkylamino, di(C$_1$–C$_8$-alkyl)amino, C$_1$–C$_8$-alkylthio, C$_2$–C$_8$-alkenylthio, or C$_3$–C$_7$-cycloalkylthio; or represent optionally halogen-, nitro-, cyano-, or C$_1$–C$_4$-alkoxy-, C$_1$–C$_4$-haloalkoxy-, C$_1$–C$_4$-alkylthio-, C$_1$–C$_4$-haloalkylthio-, C$_1$–C$_4$-alkyl-, or C$_1$–C$_4$-haloalkyl-substituted phenyl, phenoxy, or phenylthio, and
R$^6$ and R$^7$ independently of one another represent hydrogen; represent optionally halogen-substituted C$_1$–C$_8$-alkyl, C$_3$–C$_8$-cycloalkyl, C$_1$–C$_8$-alkoxy, C–C$_8$-alkenyl, or C$_1$–C$_8$-alkoxy-C$_1$–C$_8$-alkyl; represent optionally halogen-, C$_1$–C$_8$-haloalkyl-, C$_1$–C$_8$-alkyl-, or C$_1$–C$_8$-alkoxy-substituted phenyl: or represent optionally halogen-, C$_1$–C$_8$-alkyl-, C$_1$–C$_8$-haloalkyl-, or C$_1$–C$_8$-alkoxy-substituted benzyl; or R$^6$ and R$^7$ together with the nitrogen atom to which they are attached represent optionally C$_1$–C$_4$-alkyl-substituted C$_4$–C$_7$-cycloalkyl in which one carbon atom is optionally replaced by oxygen or sulphur.

2. A compound according to claim 1 in which
(a) W represents hydrogen, chlorine, bromine, C$_1$–C$_4$-alkyl, or C$_1$–C$_4$-alkoxy,
X represents chlorine, bromine, C$_1$–C$_4$-alkyl, C$_1$–C$_4$-alkoxy, C$_1$–C$_2$-haloalkyl, C$_1$–C$_2$-haloalkoxy, or cyano,
Y in the 4-position represents hydrogen, C$_1$–C$_4$-alkoxy, chlorine, bromine, cyano, or C$_1$–C$_2$-haloalkyl, and Z in the 3- or 5-position represents hydrogen or $C_1$–$C_4$-alkyl, or (b) W represents hydrogen, chlorine, bromine, or $C_1$–$C_4$-alkyl, X represents chlorine, bromine, $C_1$–$C_4$-alkyl, $C_1$–$C_4$-alkoxy, $C_1$–$C_2$-haloalkyl, $C_1$–$C_2$-haloalkoxy, or cyano, Y in the 4-position represents a radical

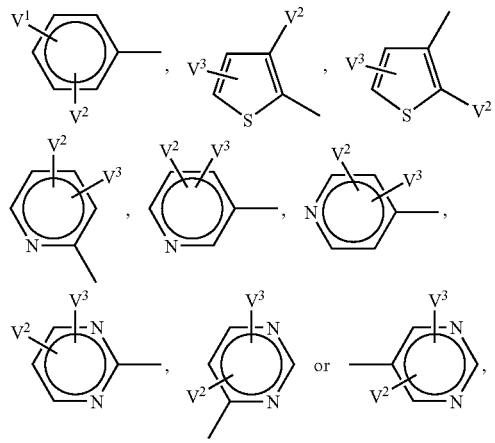

in which $V^1$ represents hydrogen, fluorine, chlorine, bromine, $C_1$–$C_6$-alkyl, $C_1$–$C_4$-alkoxy, $C_1$–$C_2$-haloalkyl, $C_1$–$C_2$-haloalkoxy, nitro, or cyano; or represents phenyl that is optionally mono- or disubstituted by fluorine, chlorine, bromine, $C_1$–$C_4$-alkyl, $C_1$–$C_4$-alkoxy, $C_1$–$C_2$-haloalkyl, $C_1$–$C_2$-haloalkoxy, nitro, or cyano, and $V^2$ and $V^3$ independently of one another represent hydrogen, fluorine, chlorine, bromine, $C_1$–$C_4$-alkyl, $C_1$–$C_4$-alkoxy, $C_1$–$C_2$-haloalkyl, or $C_1$–$C_2$-haloalkoxy, or $V^1$ and $V^2$ together represent —O—$CH_2$—O— or —O—$CF_2$—O—, and Z represents hydrogen, or (c) W represents hydrogen, chlorine, bromine, or $C_1$–$C_4$-alkyl, X represents chlorine, $C_1$–$C_4$-alkyl, or $C_1$–$C_2$-haloalkyl, Y in the 4-position represents hydrogen, $C_1$–$C_4$-alkyl, or chlorine, and Z in the 5-position represents a radical

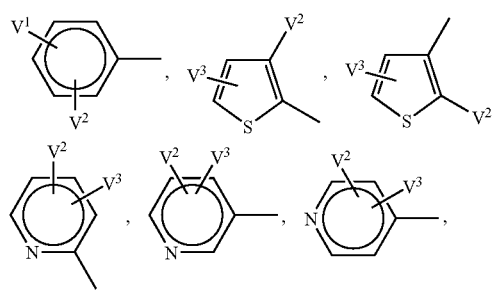

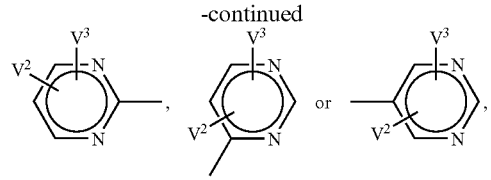

in which $V^1$ represents hydrogen, fluorine, chlorine, bromine, $C_1$–$C_6$-alkyl, $C_1$–$C_4$-alkoxy, $C_1$–$C_2$-haloalkyl, $C_1$–$C_2$-haloalkoxy, nitro, or cyano; or represents phenyl that is optionally mono- or disubstituted by fluorine, chlorine, bromine, $C_1$–$C_4$-alkyl, $C_1$–$C_4$-alkoxy, $C_1$–$C_2$-haloalkyl, $C_1$–$C_2$-haloalkoxy, nitro, or cyano, and $V^2$ and $V^3$ independently of one another represent hydrogen, fluorine, chlorine, bromine, $C_1$–$C_4$-alkyl, $C_1$–$C_4$-alkoxy, $C_1$–$C_2$-haloalkyl, or $C_1$–$C_2$-haloalkoxy, or $V^1$ and $V^2$ together represent —O—$CH_2$—O— or —O—$CF_2$—O—, or (d) W represents hydrogen, methyl, chlorine, or bromine, X represents chlorine, bromine, $C_1$–$C_4$-alkyl, $C_1$–$C_4$-alkoxy, $C_1$–$C_2$-haloalkyl, $C_1$–$C_2$-haloalkoxy, or cyano, Y in the 4-position represents hydrogen, chlorine, bromine, $C_1$–$C_4$-alkyl, $C_1$–$C_2$-haloalkyl, cyano, or $C_1$–$C_2$-haloalkoxy, and Z in the 3- or 5-position represents hydrogen, chlorine, bromine, or $C_1$–$C_4$-alkyl, and A represents hydrogen; represents $C_1$–$C_{10}$-alkyl or $C_1$–$C_8$-alkoxy-$C_1$–$C_6$-alkyl, each of which is optionally mono- to trisubstituted by fluorine or chlorine; represents $C_3$–$C_7$-cycloalkyl that is optionally mono- or disubstituted by fluorine, chlorine, $C_1$–$C_4$-alkyl, or $C_1$–$C_4$-alkoxy and in which one ring member is optionally replaced by oxygen or sulphur, B represents hydrogen or $C_1$–$C_6$-alkyl, or A, B, and the carbon atom to which they are attached represent saturated or unsaturated $C_5$–$C_7$-cycloalkyl in which one ring member is optionally replaced by oxygen or sulphur and that is optionally monosubstituted by $C_1$–$C_6$-alkyl, $C_5$–$C_8$-cycloalkyl, $C_1$–$C_3$-haloalkyl, or $C_1$–$C_6$-alkoxy, D represents hydrogen; represents $C_1$–$C_{10}$-alkyl, $C_3$–$C_6$-alkenyl, $C_1$–$C_6$-alkoxy-$C_2$–$C_4$-alkyl, or $C_1$–$C_4$-alkylthio-$C_2$–$C_4$-alkyl, each of which is optionally mono- to trisubstituted by fluorine or chlorine: represents $C_3$–$C_7$-cycloalkyl that is optionally substituted by fluorine, chlorine, $C_1$–$C_4$-alkyl, $C_1$–$C_4$-alkoxy, or $C_1$–$C_2$-haloalkyl and in which one methylene group is optionally replaced by oxygen or sulphur, and G represents hydrogen (a) or represents one of the groups (b)

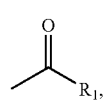

-continued

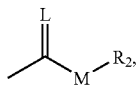 (c)

 (d)

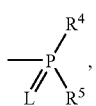 (e)

E or (f)

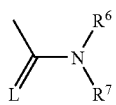 (g)

in which

E represents a metal ion equivalent or an ammonium ion,

L represents oxygen or sulphur,

M represents oxygen or sulphur, $R^1$ represents $C_1$–$C_{16}$-alkyl, $C_2$–$C_{16}$-alkenyl, $C_1$–$C_6$-alkoxy-$C_1$–$C_6$-alkyl, $C_1$–$C_4$-alkylthio-$C_1$–$C_4$-alkyl, or poly-$C_1$–$C_4$-alkoxy-$C_1$–$C_4$-alkyl, each of which is optionally mono- to trisubstituted by fluorine or chlorine; or represents $C_3$–$C_7$-cycloalkyl that is optionally mono- or disubstituted by fluorine, chlorine, $C_1$–$C_4$-alkyl, or $C_1$–$C_4$-alkoxy and in which one or two ring members that are not directly adjacent are optionally replaced by oxygen and/or sulphur; represents phenyl that is optionally mono- or disubstituted by fluorine, chlorine, bromine, cyano, nitro, $C_1$–$C_4$-alkyl, $C_1$–$C_4$-alkoxy, $C_1$–$C_3$-haloalkyl, $C_1$–$C_3$-haloalkoxy, $C_1$–$C_4$-alkylthio, or $C_1$–$C_4$-alkylsulphonyl; represents phenyl-$C_1$–$C_4$-alkyl that is optionally mono- or disubstituted by fluorine, chlorine, bromine, $C_1$–$C_4$-alkyl, $C_1$–$C_4$-alkoxy, $C_1$–$C_3$-haloalkyl, or $C_1$–$C_3$-haloalkoxy; represents pyrazolyl, thiazolyl, pyridyl, pyrimidyl, furanyl, or thienyl, each of which is optionally monosubstituted by fluorine, chlorine, bromine, or $C_1$–$C_4$-alkyl; or represents phenoxy-$C_1$–$C_3$-alkyl that is optionally mono- or disubstituted by fluorine, chlorine, bromine, or $C_1$–$C_4$-alkyl, $R^2$ represents $C_1$–$C_{16}$-alkyl, $C_2$–$C_{16}$-alkenyl, $C_1$–$C_6$-alkoxy-$C_2$–$C_6$-alkyl, or poly-$C_1$–$C_6$-alkoxy-$C_2$–$C_6$-alkyl, each of which is optionally mono- to trisubstituted by fluorine; represents $C_3$–$C_7$-cycloalkyl that is optionally mono- or disubstituted by fluorine, chlorine, $C_1$–$C_4$-alkyl, or $C_1$–$C_4$-alkoxy; or represents phenyl or benzyl, each of which is optionally mono- or disubstituted by fluorine, chlorine, bromine, cyano, nitro, $C_1$–$C_4$-alkyl, $C_1$–$C_3$-alkoxy, $C_1$–$C_3$-haloalkyl, or $C_1$–$C_3$-haloalkoxy;

$R^3$ represents $C_1$–$C_6$-alkyl that is optionally mono- to trisubstituted by fluorine; or represents phenyl or benzyl, each of which is optionally mono- or disubstituted by fluorine, chlorine, bromine, $C_1$–$C_4$-alkyl, $C_1$–$C_4$-alkoxy, $C_1$–$C_3$-haloalkyl, $C_1$–$C_3$-haloalkoxy, cyano, or nitro, $R^4$ represents $C_1$–$C_6$-alkyl, $C_1$–$C_6$-alkoxy, $C_1$–$C_6$-alkylamino, di($C_1$–$C_6$-alkyl)amino, $C_1$–$C_6$-alkylthio, $C_3$–$C_4$-alkenylthio, or $C_3$–$C_6$-cycloalkylthio; or represents phenyl, phenoxy, or phenylthio, each of which is optionally mono- or disubstituted by fluorine, chlorine, bromine, nitro, cyano, $C_1$–$C_3$-alkoxy, $C_1$–$C_3$-haloalkoxy, $C_1$–$C_3$-alkylthio, $C_1$–$C_3$-haloalkylthio, $C_1$–$C_3$-alkyl, or $C_1$–$C_3$-haloalkyl, $R^5$ represents $C_1$–$C_4$-alkoxy or $C_1$–$C_4$-alkylthio, $R^6$ represents $C_1$–$C_6$-alkyl, $C_3$–$C_6$-cycloalkyl, $C_1$–$C_6$-alkoxy, $C_3$–$C_6$-alkenyl, or $C_1$–$C_6$-alkoxy-$C_1$–$C_6$-alkyl; represents phenyl that is optionally mono- or disubstituted by fluorine, chlorine, bromine, $C_1$–$C_3$-haloalkyl, $C_1$–$C_4$-alkyl, or $C_1$–$C_4$-alkoxy; represents benzyl that is optionally mono- or disubstituted by fluorine, chlorine, bromine, $C_1$–$C_4$-alkyl, $C_1$–$C_3$-haloalkyl, or $C_1$–$C_4$-alkoxy, and $R^7$ represents hydrogen, $C_1$–$C_6$-alkyl, or $C_3$–$C_6$-alkenyl, or $R^6$ and $R^7$ together with the nitrogen atom to which they are attached represent $C_5$–$C_6$-cycloalkyl that is optionally mono- or disubstituted by methyl or ethyl and in which one methylene group is optionally replaced by oxygen or sulphur.

3. A compound according to claim 1 in which (a) W represents hydrogen, chlorine, methyl, ethyl, or methoxy, X represents chlorine, bromine, methyl, ethyl, propyl, methoxy, trifluoromethyl, difluoromethoxy, trifluoroethoxy, or cyano, Y in the 4-position represents hydrogen, methoxy, chlorine, bromine, or trifluoromethyl, and Z in the 3- or 5-position represents hydrogen or methyl, or (b) W represents hydrogen, chlorine, bromine, or methyl, X represents chlorine, bromine, methyl, ethyl, propyl, methoxy, trifluoromethyl, difluoromethoxy, or cyano, Y in the 4-position represents the radical

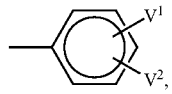

in which $V^1$ represents hydrogen, fluorine, chlorine, bromine, methyl, ethyl, n-propyl, isopropyl, tert-butyl, methoxy ethoxy, n-propoxy, isopropoxy, trifluoromethyl, or trifluoromethoxy, and $V^2$ represents hydrogen, fluorine, chlorine, methyl, ethyl, n-propyl, isopropyl, methoxy, ethoxy, or trifluoromethyl, and Z represents hydrogen, or (c) W represents hydrogen, chlorine, or methyl, X represents chlorine, methyl, or trifluoromethyl, Y in the 4-position represents hydrogen or methyl, and Z in the 5-position represents the radical

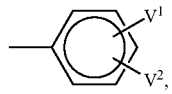

in which

V¹ represents hydrogen, fluorine, chlorine, bromine, methyl, ethyl, n-propyl, isopropyl, tert-butyl, methoxy, ethoxy, n-propoxy, isopropoxy, trifluoromethyl, or trifluoramethoxy, and V² represents hydrogen, fluorine, chlorine, methyl, ethyl, n-propyl, isopropyl, methoxy, ethoxy, or trifluoromethyl, or (d) W represents hydrogen, methyl, chlorine, or bromine, X represents chlorine, bromine, methyl, methoxy, trifluoromethyl, difluoromethoxy, trifluoromethoxy, or cyano, Y in the 4-position represents hydrogen, chlorine, bromine, methyl, trifluoromethyl, or trifluoromethoxy, and Z in the 3- or 5-position represents hydrogen, chlorine, bromine, or methyl, and A represents hydrogen, $C_1$–$C_4$-alkyl, or $C_1$–$C_4$-alkoxy-$C_1$–$C_2$-alkyl; represents $C_3$–$C_6$-cycloalkyl that is optionally monosubstituted by fluorine, methyl, ethyl, or methoxy and in which optionally one ring member is replaced by oxygen or sulphur, B represents hydrogen, methyl, or ethyl, or A, B, and the carbon atom to which they are attached represent saturated $C_5$–$C_6$-cycloalkyl in which one ring member is optionally replaced by oxygen and that is optionally monosubstituted by methyl, ethyl, propyl, isopropyl, butyl, trifluoromethyl, methoxy, ethoxy, propoxy, butoxy, or isobutoxy, D represents hydrogen; represents $C_1$–$C_8$-alkyl, $C_3$–$C_4$-alkenyl, $C_1$–$C_6$-alkoxy-$C_2$–$C_4$-alkyl, $C_1$–$C_4$-alkylthio-$C_2$–$C_4$-alkyl, or $C_3$–$C_6$-cycloalkyl, each of which is optionally mono- to trisubstituted by fluorine, and G represents hydrogen (a) or represents one of the groups

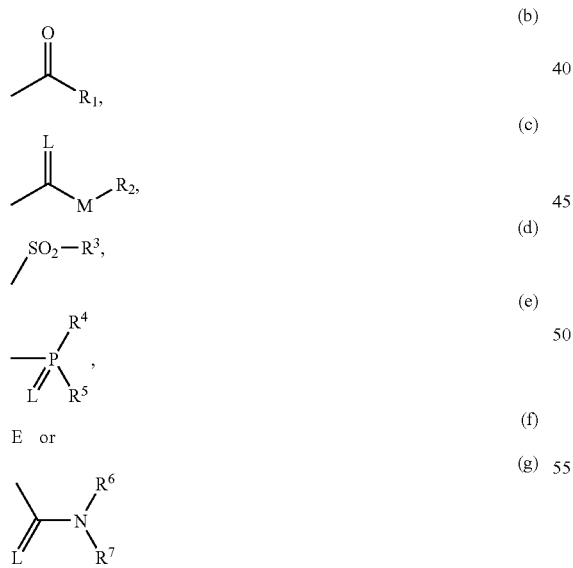

in which

E represents a metal ion equivalent or an ammonium ion,

L represents oxygen or sulphur,

M represents oxygen or sulphur,

R¹ represents $C_1$–$C_{10}$-alkyl, $C_2$–$C_{10}$-alkenyl, $C_1$–$C_2$-alkoxy-$C_1$–$C_2$-alkyl, or $C_1$–$C_2$-alkylthio-$C_1$–$C_2$-alkyl, each of which is optionally mono- to trisubstituted by fluorine or chlorine; or represents $C_3$–$C_6$-cycloalkyl that is optionally mono- or disubstituted by fluorine, chlorine, methyl, ethyl, propyl, isopropyl, butyl, i-butyl, tert-butyl, methoxy, ethoxy, n-propoxy, or isopropoxy and in which one ring member is optionally replaced by oxygen; represents phenyl that is optionally mono- or disubstituted by fluorine, chlorine, bromine, cyano, nitro, methyl, ethyl, n-propyl, isopropyl, tert-butyl, methoxy, ethoxy, trifluoromethyl, or trifluoromethoxy; represents benzyl that is optionally mono- or disubstituted by fluorine, chlorine, bromine, methyl, methoxy, trifluoromethyl, or trifluoromethoxy; or represents furanyl, thienyl, pyridyl, pyrimidyl, thiazolyl, or pyrazolyl, each of which is optionally substituted by fluorine, chlorine, bromine, methyl, or ethyl;

R² represents $C_1$–$C_{10}$-alkyl, $C_2$–$C_{10}$-alkenyl, or $C_1$–$C_4$-alkoxy-$C_2$–$C_3$-alkyl, each of which is optionally mono- to trisubstituted by fluorine; represents $C_3$–$C_6$-cycloalkyl that is optionally monosubstituted by fluorine, chlorine, methyl, ethyl, or methoxy; or represents phenyl or benzyl, each of which is optionally monosubstituted by fluorine, chlorine, cyano, nitro, methyl, ethyl, n-propyl, isopropyl, methoxy, ethoxy, trifluoromethyl, or trifluoromethoxy, R³ represents methyl, ethyl, or n-propyl; or represents phenyl that is optionally monosubstituted by fluorine, chlorine, bromine, methyl, tert-butyl, methoxy, trifluoromethyl, trifluoromethoxy, cyano, or nitro, R⁴ represents $C_1$–$C_4$-alkyl, $C_1$–$C_4$-alkoxy, $C_1$–$C_4$-alkylamino, di($C_1$–$C_4$-alkyl)amino, or $C_1$–$C_4$-alkylthio; or represents phenoxy or phenylthio, each of which is optionally monosubstituted by fluorine, chlorine, bromine, nitro, cyano, $C_1$–$C_2$-alkoxy, $C_1$–$C_2$-fluoroalkoxy, $C_1$–$C_2$-alkylthio, $C_1$–$C_2$-fluoroalkylthio, or $C_1$–$C_3$-alkyl, R⁵ represents methoxy, ethoxy, methylthio, or ethylthio, R⁶ represents $C_1$–$C_4$-alkyl, $C_3$–$C_6$-cycloalkyl, $C_1$–$C_4$-alkoxy, $C_3$–$C_4$-alkenyl, or $C_1$–$C_4$-alkoxy-$C_1$–$C_4$-alkyl; represents phenyl that is optionally mono- or disubstituted by fluorine, chlorine, bromine, trifluoromethyl, methyl, or methoxy; or represents benzyl that is optionally monosubstituted by fluorine, chlorine, bromine, methyl, trifluoromethyl, or methoxy, and R⁷ represents hydrogen, methyl, ethyl, propyl, isopropyl, butyl, or allyl, or R⁶ and R⁷ together with the nitrogen atom to which they are attached represent $C_5$–$C_6$-cycloalkyl that is optionally mono- or disubstituted by methyl and in which one methylene group is optionally replaced by oxygen.

4. A compound according to claim 1 in which (a) W represents hydrogen, methyl, ethyl, or chlorine, X represents methyl or chlorine, Y in the 4-position represents methoxy, chlorine, bromine, or trifluoromethyl, Z in the 5-position represents hydrogen or methyl, A represents methyl, B represents methyl, D represents methyl or hydrogen, and
G represents hydrogen, or (b) W represents hydrogen,
X represents methyl or chlorine,
Y represents hydrogen,
Z in the 5-position represents

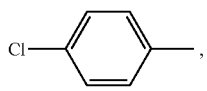,

A represents methyl,
B represents methyl, or
A and B together represent $(CH_2)_3$—,
D represents methyl, and
G represents hydrogen (a) or represents one of the groups

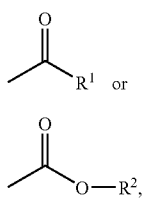

in which
$R^1$ represents $C_1$–$C_6$-alkyl, and
$R^2$ represents $C_1$–$C_6$-alkyl, or (c) W represents hydrogen or methyl,
X represents methyl or bromine,
Y in the 4-position represents methyl,
Z in the 3- or 5-position represents methyl or hydrogen,
A moreover represents methyl,
B moreover represents methyl, or
A and B together represent —$(CH_2)_4$—,
D represents methyl, and
G represents hydrogen (a) or represents one of the groups

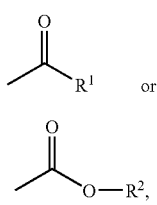

in which
$R^1$ represents $C_1$–$C_6$-alkyl, and
$R^2$ represents $C_1$–$C_6$-alkyl.

5. A process for preparing compounds according to claim 1 comprising
(A) for compounds of formula (I-a)

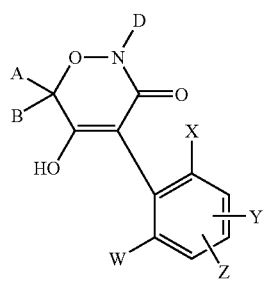

in which A, B, D, W, X, Y, and Z are as defined in claim 1,
intramolecularly condensing an N-acylhydroxyamino acid ester of formula (II)

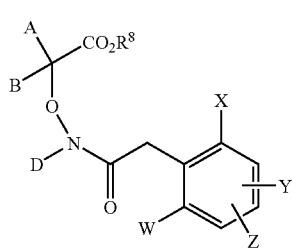

in which
A, B, D, W, X, Y, and Z are as defined in claim 1, and
$R^8$ represents alkyl,
in the presence of a diluent and in the presence of a base;
(B) for compounds of the formula (I-b)

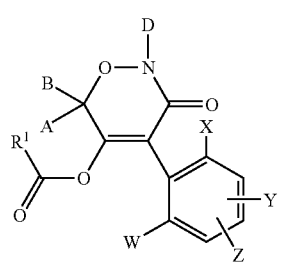

in which A, B, D, $R^1$, W, X, Y, and Z are as defined in claim 1,
reacting a compound of formula (I-a), in which A, B, D, W, X, Y and Z are as defined in claim 1,
(α) with an acid halide of formula (III)

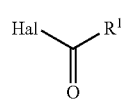

in which

R¹ is as defined in claim 1, and
Hal represents halogen,
or
(β) with a carboxylic anhydride of formula (IV)

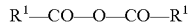  (IV)

in which R¹ is as defined in claim 1,
optionally in the presence of a diluent and optionally in the presence of an acid binder;
(C) for compounds of formula (I-c)

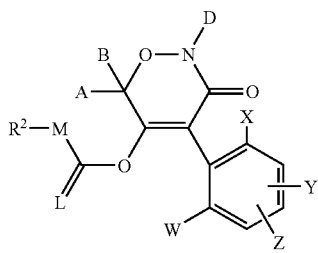 (I-c)

in which
A, B, D, R², M, W, X, Y, and Z are as defined in claim 1, and
L represents oxygen,
reacting a compound of formula (I-a), in which A, B, D, W, X, Y, and Z are as defined in claim 1,
with a chloroformic ester or chloroformic thioester of formula (V)

R²-M-CO—Cl    (V)

in which R² and M are as defined in claim 1, optionally in the presence of a diluent and optionally in the presence of an acid binder;
(D) for compounds of formula (I-c)

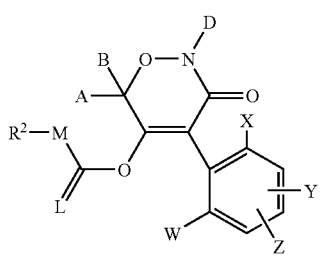 (I-c)

in which
A, B, D, R², M, W, X, Y, and Z are as defined in claim 1, and
L represents sulphur,
reacting a compound of formula (I-a), in which A, B, D, W, X, Y, and Z are as defined in claim 1,
with a chloromonothioformic ester or chlorodithioformic ester of formula (VI)

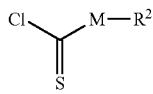 (VI)

in which M and R² am as defined in claim 1,
optionally in the presence of a diluent and optionally in the presence of an acid binder;
(E) for compounds of formula (I-d)

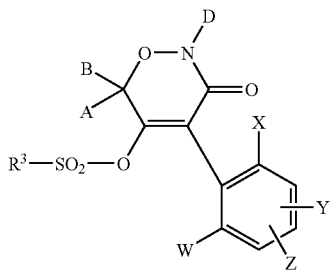 (I-d)

in which A, B, D, R³, W, X, Y, and Z are as defined in claim 1,
reacting a compound of formula (I-a), in which A, B, D, W, X, Y, and Z are as defined in claim 1,
with a sulphonyl chloride of formula (VII)

R³—SO₂—Cl    (VII)

in which R³ is as defined in claim 1,
optionally in the presence of a diluent and optionally in the presence of an acid binder,
(F) for compounds of the formula (I-e)

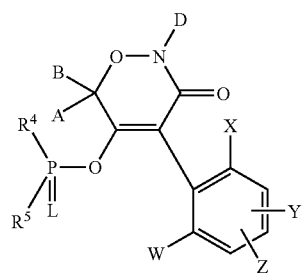 (I-e)

in which A, B, D, L, R⁴, R⁵, W, X, Y, and Z are as defined in claim 1,
reacting a compound of formula (I-a) in which A, B, D, W, X, Y, and Z are as defined in claim 1,
with a phosphorus compound of formula (VIII)

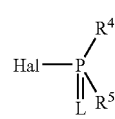 (VIII)

in which
L, R⁴, and R⁵ are as defined in claim 1, and
Hal represents halogen,
optionally in the presence of a diluent and optionally in the presence of an acid binder, (G) for compounds of formula (I-f)

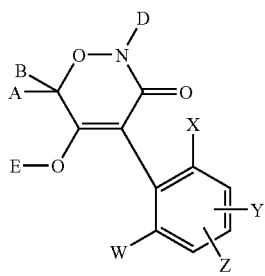
(I-f)

in which A, B, D, E, W, X, Y and Z are as defined in claim 1, reacting a compound of formula (I-a), in which A, B, D, W, X, Y, and Z are as defined in claim 1, with a metal compound of formula (IX)

$$Me(OR10)_t \quad (IX)$$

in which

Me represents a mono- or divalent metal, t represents the number 1 or 2, and $R^{10}$ represents hydrogen or alkyl, or an amine of formula (X)

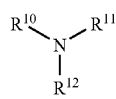
(X)

in which $R^{11}$ and $R^{12}$ independently of one another represent hydrogen or alkyl, optionally in the presence of a diluent, (H) for compounds of the formula (I-g)

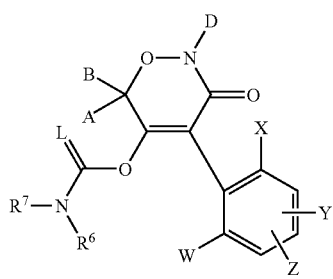
(I-g)

in which A, B, D, L, $R^6$, $R^7$, W, X, Y and Z are as defined in claim 1, reacting a compound of formula (I-a), in which A, B, D, W, X, V, and Z are as defined in claim 1, (α) with an isocyanate or isothiocyanate of formula (XI)

$$R^6{-}N{=}C{=}L \quad (XI)$$

in which $R^6$ and L are as defined in claim 1, optionally in the presence of a diluent and optionally in the presence of a catalyst, or (β) with a carbamoyl chloride or thiocarbamoyl chloride of formula (XII)

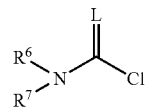
(XII)

in which L, $R^6$, and $R^7$ are as defined in claim 1, optionally in the presence of a diluent and optionally in the presence of an acid binder.

6. A compound of formula (II)

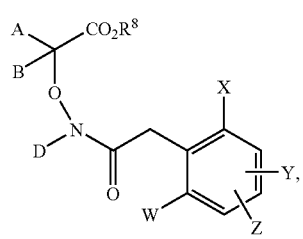
(II)

in which (a) W represents hydrogen, halogen, alkyl, or alkoxy,
X represents halogen, alkyl, alkoxy, haloalkyl, haloalkoxy or cyano,
Y in the 4-position represents hydrogen, alkoxy, halogen, cyano, or haloalkyl, and
Z in the 3- or 5-position represents hydrogen or alkyl, or (b) W represents hydrogen, halogen, or alkyl,
X represents halogen, alkyl, alkoxy, haloalkyl, haloalkoxy or cyano,
Y in the 4-position represents optionally substituted aryl or hetaryl, and
Z represents hydrogen, or (c) W represents hydrogen, halogen, or alkyl,
X represents halogen, alkyl, alkoxy, haloalkyl, haloalkoxy or cyano,
Y in the 4-position represents hydrogen, alkyl, or halogen, and
Z in the 5-position represents optionally substituted aryl or hetaryl, or (d) W represents hydrogen, methyl, propyl, isopropyl, or halogen,
X represents halogen, alkyl, alkoxy, haloalkyl, haloalkoxy or cyano,
Y in the 4-position represents hydrogen, halogen, alkyl, haloalkyl, cyano, or haloalkoxy, and
Z in the 3- or 5-position moreover represents hydrogen, halogen, or alkyl, and A represents hydrogen; represents optionally halogen-substituted alkyl, alkenyl, alkoxyalkyl, polyalkoxyalkyl, or alkylthioalkyl; or represents saturated or unsaturated optionally substituted cycloalkyl in which one or more ring atoms are optionally replaced by a heteroatam, B represents hydrogen, alkyl, or alkoxyalkyl, or A and B together with the carbon atom to which they are attached represent a saturated or unsaturated unsubstituted or substituted cycle that optionally contains one or more heteroatoms, D represents hydrogen or an optionally substituted radical selected from the group consisting of alkyl, alkenyl, alkoxyalkyl, polyalkoxyalkyl, alkylthioalkyl, and saturated or unsaturated cycloalkyl in which one or more ring members are optionally replaced by heteroatoms, and $R^8$ represents alkyl.

7. A pesticide, microbicide, or herbicide composition comprising one or more compounds according to claim 1 and one or more extenders and/or surfactants.

8. A method for controlling animal pests comprising allowing an effective amount of one or more compounds according to claim 1 to act on animal pests and/or their habitat.

9. A method for controlling unwanted vegetation comprising allowing an effective amount of one or more compounds according to claim 1 to act on unwanted vegetation and/or their habitat.

10. A method for controlling fungi comprising allowing an effective amount of one or more compounds according to claim 1 to act on fungi and/or their habitat.

11. A process for preparing a pesticide, microbicide, or herbicide composition comprising mixing one or more compounds according to claim 1 with one or more extenders and/or surfactants.

* * * * *